US008114668B2

(12) United States Patent
Stolen et al.

(10) Patent No.: US 8,114,668 B2
(45) Date of Patent: Feb. 14, 2012

(54) COMPOSITION FOR COLD STORAGE OF STEM CELLS

(75) Inventors: Craig Stolen, New Brighton, MN (US); Steven D. Girouard, Chagrin Falls, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 976 days.

(21) Appl. No.: 11/748,315

(22) Filed: May 14, 2007

(65) Prior Publication Data

US 2008/0286324 A1 Nov. 20, 2008

(51) Int. Cl.
*C12N 5/00* (2006.01)
(52) U.S. Cl. ............ 435/374; 435/1.1; 435/1.3; 435/366
(58) Field of Classification Search .................. None
See application file for complete search history.

(56) References Cited

U.S. PATENT DOCUMENTS

| | | | |
|---|---|---|---|
| 6,120,805 A | 9/2000 | Spenlehauer et al. | |
| 6,277,557 B1 | 8/2001 | Burger et al. | |
| 6,287,628 B1 | 9/2001 | Hossainy et al. | |
| 6,506,437 B1 | 1/2003 | Harish et al. | |
| 6,544,582 B1 | 4/2003 | Yoe | |
| 6,555,157 B1 | 4/2003 | Hossainy | |
| 6,585,765 B1 | 7/2003 | Hossainy et al. | |
| 6,616,765 B1 | 9/2003 | Castro et al. | |
| 6,630,486 B1 | 10/2003 | Royer | |
| 6,787,353 B1 | 9/2004 | Rao et al. | |
| 7,037,482 B2 | 5/2006 | Saito et al. | |
| 2003/0091545 A1 | 5/2003 | Mineau-Hanschke | |
| 2004/0091498 A1 | 5/2004 | Zhang et al. | |
| 2005/0089836 A1 | 4/2005 | Murphy et al. | |
| 2006/0127373 A1* | 6/2006 | Son et al. ........... | 424/93.7 |
| 2006/0193885 A1 | 8/2006 | Leonard Neethling et al. | |
| 2006/0234376 A1 | 10/2006 | Mistry et al. | |
| 2006/0239985 A1 | 10/2006 | Croissant et al. | |

FOREIGN PATENT DOCUMENTS

| | | |
|---|---|---|
| EP | 1652538 A2 | 5/2006 |
| JP | 2005154338 | 6/2005 |
| WO | WO-00/27996 A1 | 5/2000 |
| WO | WO-02/09738 A1 | 2/2002 |
| WO | WO-2005/056755 A2 | 6/2005 |
| WO | WO-2005/120549 A2 | 12/2005 |
| WO | WO-2008/143884 A2 | 11/2008 |

OTHER PUBLICATIONS

"International Application Serial No. PCT/US2008/006164, International Search Report mailed Jul. 21, 2009", 5 pgs.
"International Application Serial No. PCT/US2008/006164, Written Opinion mailed Jul. 21, 2009", 9 pgs.
Ambiru, S., et al., "Improved survival of orthotopic liver allograft in swine by addition of trophic factors to University of Wisconsin solution.", *Transplantation*, 77(2), (Jan. 2004), 302-19.
Furue, M., et al., "Leukemia inhibitory factor as an anti-apoptotic mitogen for pluripotent mouse embryonic stem cells in a serum-free medium without feeder cells", In *Vitro Cellular & Develipmental Biology—Animal*, vol. 41, No. 1-2,, 2005, 19-28.
Gennaro, R., et al., "Structural Features and Biological Activities of the Cathelicidin-Derived Antimicroobial Preparations", *Biopoly.*, 55, (2000), 31-49.
Greiner, A., et al., "Biohybrid nanosystems with polymer nanofibers and nanotubes", *Appl. Microbiol. Biotechnol.*, 71, (2006), 387-393.
Heese, K., et al., "Nerve Growth Factor, Neural Stem Cells and Alzheimer's Disease", *Neurosignals*, 15(1), (2006/2007), 1-12.
Kang, H. S., et al., "Neurokinin receptors: relevance to the emerging immune system", *Archivum Immunologiae et Therapiae Experimentals*, 52(5), (2004), 338-347.
Klüver, E., et al., "Synthesis and structure—activity relationship of β-defensins, multi-functional peptides of the immune system", *Journal of Peptide Science*, 12, (2006), 243-357.
Laiuppa, J. A., et al., "Culture materials affect ex vivo expansion of hematopoietic progenitor cells", *J. Biomed. Mater. Res.*, 36(3), (1997), 347-359.
Lebrun, B., et al., "Brain-derived neurotrophic factor (BDNF) and food intake regulation: A minireview", *Autonomic Neuroscience: Basic and Clinical*, 126-127., (2006), 30-38.
Lee, K.-H., "Structure Activity Relationship Study and Recent Advances in the Design and Synthesis about Linear Antimicrobial Peptides", *Current Medicinal Chemistry—Anti-Infective Agents*, 1(3), (2002), 305-318.
Makino, H., et al., "Immobilization of Leukemia Inhibitory Factor (LIF) to Culture Murine Embryonic Stem Cells", *Journal of Bioscience and Bioengineering*, 98(5), (2004), 374-379.
McAnulty, J. F., et al., "Successful Six-Day Kidney Preservation Using Trophic Factor Supplemented Media and Simple Cold Storage", *Am Journal of Transplantation*, 2(8), (Sep. 2002), 712-718.
McAnulty, J. F., et al., "Suppression of cold ischemic injury in stored kidneys by the antimicrobial peptide bactenecin", *Cryobiology*, 49(3), (Dec. 2004), 230-240.
Murphy, C. J., et al., "Trophic Factors Modulate Signal Transduction Pathways in Cold-Stored Kidney Cells", *American Society of Cell Biology Meeting*, San Francisco, CA, Presentation No. 1568, Poster Board No. B31, (Abstract Only), (Dec. 2003), 1 pg.
Pazgier, M., et al., "Human β-defensins", *Cell. Mol. Life Sci.*, 63, (2006), 1294-1313.
Peleshok, J., et al., "Functional mimetics of neurotrophins and their receptors", *Biochemical Society Transactions*, 34(Part 4), (2006), 612-617.
Rawat, M., et al., "Nanocarriers: Promising Vehicle for Bioactive Drugs", *Biol. Pharm. Bull.*, 29(9), (2006), 1790-1798.
Robinson, S., et al., "Ex vivo expansion of umbilical cord blood", *Cytotherapy*, 7(3), (2005), 243-250.
Satake, H., et al., "Overview of the Primary Structure, Tissue-Distribution, and Functions of Tachykinins and their Receptors", *Current Drug Targets*, 7, (2006), 963-974.
Sieber-Blum, M, "Growth Factor Synergism and Antagonism in Early Neural Crest Development", *Biochemistry and Cell Biology*, 76(6), (1998), 1039-1050.
Ulloa-Montoya, F., et al., "Culture Systems for Pluripotent Stem Cells", *Journal of Bioscience and Bioengineering*, 100(1), (2005), 12-27.
Van Hoof, D., et al., "Embryonic stem cell proteomics", *Expert Rev. Proteomics*, 3(4), (2006), 427-437.

(Continued)

Primary Examiner — Blaine Lankford, Jr.
(74) Attorney, Agent, or Firm — Schwegman, Lundberg & Woessner, P.A.

(57) ABSTRACT

The invention provides a composition for cold storage of cells which includes a population of isolated stem cells, a cell medium, and isolated trophic factors, as well as devices having a plurality of the trophic factors.

15 Claims, 3 Drawing Sheets

OTHER PUBLICATIONS

Walsh, D. A., et al., "Tachykinins and the Cardiovascular System", *Current Drug Targets*, 7(8), (2006), 1031-1042.

Yih, T. C., et al., "Engineered Nanoparticles as Precise Drug Delivery Systems", *Journal of Cellular Biochemistry*, 97(6), (2006), 1184-1190.

Zhang, Y., et al., "Tachykinins in the Immune System", *Current Drug Targets*, 7(8), (2006), 1011-1020.

Khawaja, A. M, et al., "Abstract—Tachykinins: receptor to effector", Int J Biochem Cell Biol., 28(7), (Jul. 1996), 721-38.

McDonald, N. Q, et al., "Structural determinants of neurotrophin action", J Biol Chem., 270(34), (Aug. 25, 1995), 19669-72.

Schauber, J., et al., "Antimicrobial peptides and the skin immune defense system", J Allergy Clin Immunol., 122(2), (Aug. 2008), 261-6.

Tettamanti, G., et al., "Abstract—Phylogenesis of brain-derived neurotrophic factor (BDNF) in vertebrates", Gene, 450(1-2), (Jan. 15, 2010), 85-93.

Wiesmann, C., et al., "Abstract—Nerve growth factor: structure and function", Cell Mol Life Sci., 58(5-6), (May 2001), 748-59.

Zanetti, M., "The role of cathelicidins in the innate host defenses of mammals", Curr Issues Mol Biol., 7(2), (Jul. 2005), 179-96.

* cited by examiner

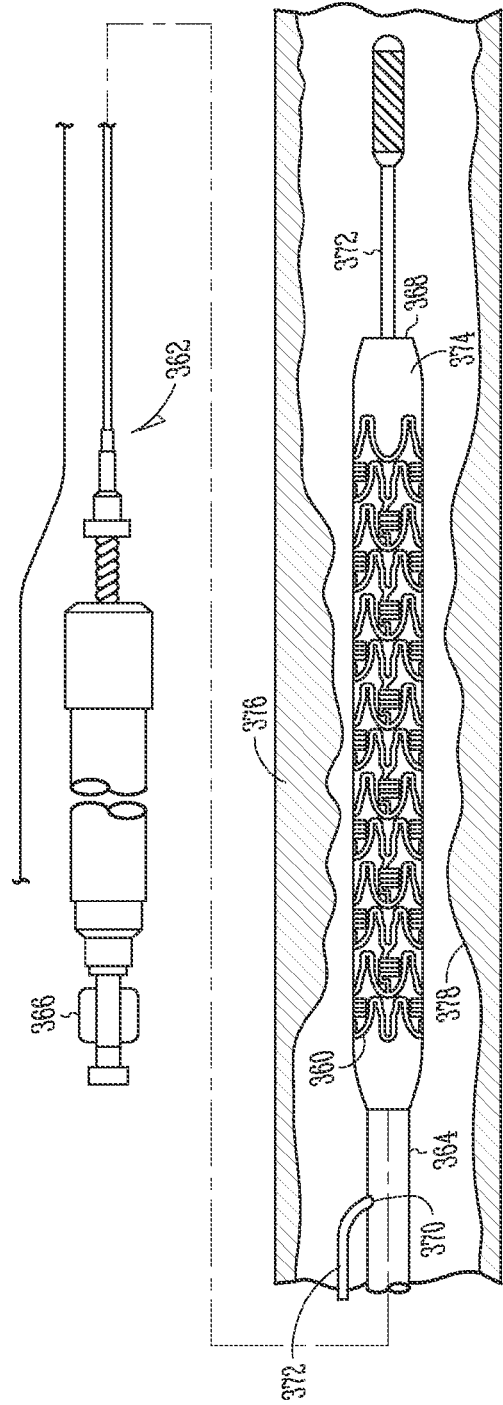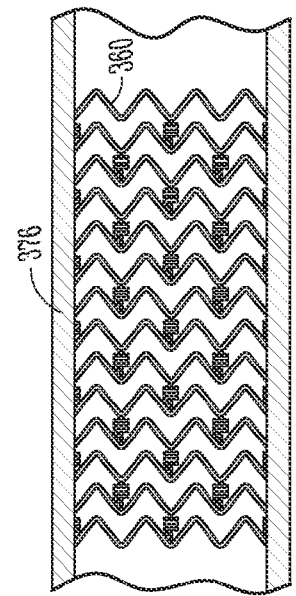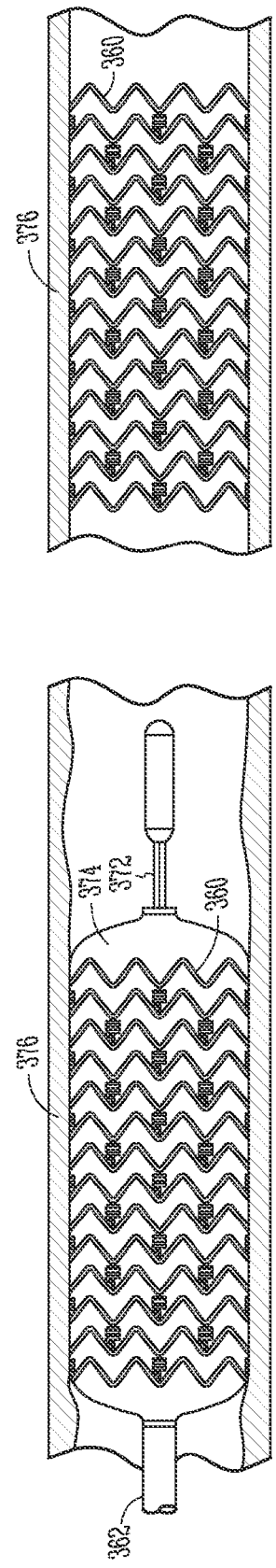
Fig. 3
Fig. 4
Fig. 5

SEQUENCE LISTING

<160> NUMBER OF SEQ ID NOS: 130

<210> SEQ ID NO 1
<211> LENGTH: 23
<212> TYPE: PRT
<213> ORGANISM: Artificial Sequence
<220> FEATURE:
<223> OTHER INFORMATION: A synthetic defense peptide

<400> SEQUENCE: 1

Gly Ile Gly Lys Phe Leu His Ser Ala Lys Lys Phe Gly Lys Ala Phe
1 5 10 15

Val Gly Glu Ile Met Asn Ser
20

<210> SEQ ID NO 2
<211> LENGTH: 37
<212> TYPE: PRT
<213> ORGANISM: Artificial Sequence
<220> FEATURE:
<223> OTHER INFORMATION: A synthetic defense peptide

<400> SEQUENCE: 2

Lys Trp Lys Leu Phe Lys Lys Ile Glu Lys Val Gly Gln Asn Ile Arg
1 5 10 15

Asp Gly Ile Ile Lys Ala Gly Pro Ala Val Ala Val Val Gly Gln Ala
20 25 30

Thr Gln Ile Ala Lys
35

<210> SEQ ID NO 3
<211> LENGTH: 26
<212> TYPE: PRT
<213> ORGANISM: Artificial Sequence
<220> FEATURE:
<223> OTHER INFORMATION: A synthetic defense peptide

<400> SEQUENCE: 3

Gly Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 4
<211> LENGTH: 33

```
<212> TYPE: PRT
<213> ORGANISM: Artificial Sequence
<220> FEATURE:
<223> OTHER INFORMATION: A synthetic defense peptide

<400> SEQUENCE: 4

Gly Phe Phe Ala Leu Ile Pro Lys Ile Ile Ser Ser Pro Lys Phe Lys
 1               5                  10                  15

Thr Leu Leu Ser Ala Val Gly Ser Ala Leu Ser Ser Ser Gly Glu Gln
            20                  25                  30

Glu

<210> SEQ ID NO 5
<211> LENGTH: 37
<212> TYPE: PRT
<213> ORGANISM: Artificial Sequence
<220> FEATURE:
<223> OTHER INFORMATION: A synthetic defense peptide

<400> SEQUENCE: 5

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 6
<211> LENGTH: 39
<212> TYPE: PRT
<213> ORGANISM: Artificial Sequence
<220> FEATURE:
<223> OTHER INFORMATION: A synthetic defense peptide

<400> SEQUENCE: 6

Arg Arg Arg Pro Arg Pro Pro Tyr Leu Pro Arg Pro Arg Pro Pro Pro
 1               5                  10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 7
<211> LENGTH: 13
<212> TYPE: PRT
<213> ORGANISM: Artificial Sequence
<220> FEATURE:
<223> OTHER INFORMATION: A synthetic defense peptide

<400> SEQUENCE: 7

Ile Leu Pro Trp Lys Trp Pro Trp Trp Pro Trp Arg Arg
 1               5                  10

<210> SEQ ID NO 8
<211> LENGTH: 24
<212> TYPE: PRT
<213> ORGANISM: Artificial Sequence
<220> FEATURE:
<223> OTHER INFORMATION: A synthetic defense peptide

<400> SEQUENCE: 8

Phe Leu Pro Leu Leu Ala Gly Leu Ala Ala Asn Phe Leu Pro Lys Ile
 1               5                  10                  15

Phe Cys Lys Ile Thr Arg Lys Cys
```

```
<210> SEQ ID NO 9
<211> LENGTH: 12
<212> TYPE: PRT
<213> ORGANISM: Artificial Sequence
<220> FEATURE:
<223> OTHER INFORMATION: A synthetic defense peptide

<400> SEQUENCE: 9

Arg Leu Cys Arg Ile Val Val Ile Arg Val Cys Arg
1               5                   10

<210> SEQ ID NO 10
<211> LENGTH: 17
<212> TYPE: PRT
<213> ORGANISM: Artificial Sequence
<220> FEATURE:
<223> OTHER INFORMATION: A synthetic defense peptide

<400> SEQUENCE: 10

Lys Trp Cys Phe Arg Val Cys Tyr Arg Gly Ile Cys Tyr Arg Arg Cys
1               5                   10                  15

Arg

<210> SEQ ID NO 11
<211> LENGTH: 18
<212> TYPE: PRT
<213> ORGANISM: Artificial Sequence
<220> FEATURE:
<223> OTHER INFORMATION: A synthetic defense peptide

<400> SEQUENCE: 11

Arg Gly Gly Arg Leu Cys Tyr Cys Arg Arg Arg Phe Cys Val Cys Val
1               5                   10                  15

Gly Arg

<210> SEQ ID NO 12
<211> LENGTH: 30
<212> TYPE: PRT
<213> ORGANISM: Artificial Sequence
<220> FEATURE:
<223> OTHER INFORMATION: A synthetic defense peptide

<400> SEQUENCE: 12

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 13
<211> LENGTH: 40
<212> TYPE: PRT
<213> ORGANISM: Artificial Sequence
<220> FEATURE:
<223> OTHER INFORMATION: A synthetic defense peptide

<400> SEQUENCE: 13

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40
```

```
<210> SEQ ID NO 14
<211> LENGTH: 64
<212> TYPE: PRT
<213> ORGANISM: Artificial Sequence
<220> FEATURE:
<223> OTHER INFORMATION: A synthetic peptide

<400> SEQUENCE: 14

Met Arg Leu His His Leu Leu Leu Ala Leu Leu Phe Leu Val Leu Ser
 1               5                  10                  15

Ala Gly Ser Gly Phe Thr Gln Gly Val Arg Asn Ser Gln Ser Cys Arg
            20                  25                  30

Arg Asn Lys Gly Ile Cys Val Pro Ile Arg Cys Pro Gly Ser Met Arg
        35                  40                  45

Gln Ile Gly Thr Cys Leu Gly Ala Gln Val Lys Cys Cys Arg Arg Lys
    50                  55                  60

<210> SEQ ID NO 15
<211> LENGTH: 24
<212> TYPE: PRT
<213> ORGANISM: Artificial Sequence
<220> FEATURE:
<223> OTHER INFORMATION: A synthetic peptide

<400> SEQUENCE: 15

Gly Val Leu Ser Asn Val Ile Gly Tyr Leu Lys Lys Leu Gly Thr Gly
 1               5                  10                  15

Ala Leu Asn Ala Val Leu Lys Gln
            20

<210> SEQ ID NO 16
<211> LENGTH: 81
<212> TYPE: PRT
<213> ORGANISM: Artificial Sequence
<220> FEATURE:
<223> OTHER INFORMATION: A synthetic peptide

<400> SEQUENCE: 16

Met Tyr Lys Gly Ile Phe Leu Cys Val Leu Leu Ala Val Ile Cys Ala
 1               5                  10                  15

Asn Ser Leu Ala Thr Pro Ser Ser Asp Ala Asp Glu Asp Asn Asp Glu
            20                  25                  30

Val Glu Arg Tyr Val Arg Gly Trp Ala Ser Lys Ile Gly Gln Thr Leu
        35                  40                  45

Gly Lys Ile Ala Lys Val Gly Leu Lys Glu Leu Ile Gln Pro Lys Arg
    50                  55                  60

Glu Ala Met Leu Arg Ser Ala Glu Ala Gln Gly Lys Arg Pro Trp Ile
65                  70                  75                  80

Leu

<210> SEQ ID NO 17
<211> LENGTH: 303
<212> TYPE: PRT
<213> ORGANISM: Artificial Sequence
<220> FEATURE:
<223> OTHER INFORMATION: A synthetic peptide

<400> SEQUENCE: 17

Met Phe Lys Gly Leu Phe Ile Cys Ser Leu Ile Ala Val Ile Cys Ala
 1               5                  10                  15

Asn Ala Leu Pro Gln Pro Glu Ala Ser Ala Asp Glu Asp Met Asp Glu
            20                  25                  30
```

```
Arg Glu Val Arg Gly Ile Gly Lys Phe Leu His Ser Ala Gly Lys Phe
             35                  40                  45

Gly Lys Ala Phe Val Gly Glu Ile Met Lys Ser Lys Arg Asp Ala Glu
 50                  55                  60

Ala Val Gly Pro Glu Ala Phe Ala Asp Glu Asp Leu Asp Glu Arg Glu
 65                  70                  75                  80

Val Arg Gly Ile Gly Lys Phe Leu His Ser Ala Lys Lys Phe Gly Lys
                 85                  90                  95

Ala Phe Val Gly Glu Ile Met Asn Ser Lys Arg Asp Ala Glu Ala Val
                100                 105                 110

Gly Pro Glu Ala Phe Ala Asp Glu Asp Leu Asp Glu Arg Glu Val Arg
             115                 120                 125

Gly Ile Gly Lys Phe Leu His Ser Ala Lys Lys Phe Gly Lys Ala Phe
            130                 135                 140

Val Gly Glu Ile Met Asn Ser Lys Arg Asp Ala Glu Ala Val Gly Pro
145                 150                 155                 160

Glu Ala Phe Ala Asp Glu Asp Leu Asp Glu Arg Glu Val Arg Gly Ile
                165                 170                 175

Gly Lys Phe Leu His Ser Ala Lys Lys Phe Gly Lys Ala Phe Val Gly
            180                 185                 190

Glu Ile Met Asn Ser Lys Arg Asp Ala Glu Ala Val Gly Pro Glu Ala
            195                 200                 205

Phe Ala Asp Glu Asp Phe Asp Glu Arg Glu Val Arg Gly Ile Gly Lys
210                 215                 220

Phe Leu His Ser Ala Lys Lys Phe Gly Lys Ala Phe Val Gly Glu Ile
225                 230                 235                 240

Met Asn Ser Lys Arg Asp Ala Glu Ala Val Gly Pro Glu Ala Phe Ala
                245                 250                 255

Asp Glu Asp Leu Asp Glu Arg Glu Val Arg Gly Ile Gly Lys Phe Leu
            260                 265                 270

His Ser Ala Lys Lys Phe Gly Lys Ala Phe Val Gly Glu Ile Met Asn
            275                 280                 285

Ser Lys Arg Asp Ala Glu Ala Val Asp Asp Arg Arg Trp Val Glu
            290                 295                 300

<210> SEQ ID NO 18
<211> LENGTH: 17
<212> TYPE: PRT
<213> ORGANISM: Artificial Sequence
<220> FEATURE:
<223> OTHER INFORMATION: A synthetic peptide

<400> SEQUENCE: 18

Lys Trp Cys Phe Arg Val Cys Tyr Arg Gly Ile Cys Tyr Arg Arg Cys
 1               5                  10                  15

Arg

<210> SEQ ID NO 19
<211> LENGTH: 17
<212> TYPE: PRT
<213> ORGANISM: Artificial Sequence
<220> FEATURE:
<223> OTHER INFORMATION: A synthetic peptide

<400> SEQUENCE: 19

Arg Trp Cys Phe Arg Val Cys Tyr Arg Gly Ile Cys Tyr Arg Lys Cys
 1               5                  10                  15
```

Arg

<210> SEQ ID NO 20
<211> LENGTH: 129
<212> TYPE: PRT
<213> ORGANISM: Artificial Sequence
<220> FEATURE:
<223> OTHER INFORMATION: A synthetic peptide

<400> SEQUENCE: 20

Met Ser Gly Arg Gly Lys Gln Gly Gly Lys Val Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Gln Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Val Arg Asn Asp Glu Glu Leu Asn Lys
                85                  90                  95

Leu Leu Gly Gly Val Thr Ile Ala Gln Gly Gly Val Leu Pro Asn Ile
            100                 105                 110

Gln Ala Val Leu Leu Pro Lys Thr Glu Ser Ser Lys Pro Ala Lys Ser
        115                 120                 125

Lys

<210> SEQ ID NO 21
<211> LENGTH: 21
<212> TYPE: PRT
<213> ORGANISM: Artificial Sequence
<220> FEATURE:
<223> OTHER INFORMATION: A synthetic peptide

<400> SEQUENCE: 21

Thr Arg Ser Ser Arg Ala Gly Leu Gln Phe Pro Val Gly Arg Val His
1               5                   10                  15

Arg Leu Leu Arg Lys
            20

<210> SEQ ID NO 22
<211> LENGTH: 63
<212> TYPE: PRT
<213> ORGANISM: Artificial Sequence
<220> FEATURE:
<223> OTHER INFORMATION: A synthetic peptide

<400> SEQUENCE: 22

Met Asn Phe Val Arg Ile Leu Ser Phe Val Phe Ala Leu Val Leu Ala
1               5                   10                  15

Leu Gly Ala Val Ser Ala Ala Pro Glu Pro Arg Trp Lys Leu Phe Lys
            20                  25                  30

Lys Ile Glu Lys Val Gly Arg Asn Val Arg Asp Gly Leu Ile Lys Ala
        35                  40                  45

Gly Pro Ala Ile Ala Val Ile Gly Gln Ala Lys Ser Leu Gly Lys
    50                  55                  60

<210> SEQ ID NO 23
<211> LENGTH: 63
<212> TYPE: PRT

```
<213> ORGANISM: Artificial Sequence
<220> FEATURE:
<223> OTHER INFORMATION: A synthetic peptide

<400> SEQUENCE: 23

Met Asn Phe Ala Lys Ile Leu Ser Phe Val Ala Leu Val Leu Ala
1               5                   10                  15

Leu Ser Met Thr Ser Ala Ala Pro Glu Pro Arg Trp Lys Ile Phe Lys
            20                  25                  30

Lys Ile Glu Lys Met Gly Arg Asn Ile Arg Asp Gly Ile Val Lys Ala
        35                  40                  45

Gly Pro Ala Ile Glu Val Leu Gly Ser Ala Lys Ala Ile Gly Lys
    50                  55                  60

<210> SEQ ID NO 24
<211> LENGTH: 63
<212> TYPE: PRT
<213> ORGANISM: Artificial Sequence
<220> FEATURE:
<223> OTHER INFORMATION: A synthetic peptide

<400> SEQUENCE: 24

Met Asn Phe Tyr Lys Ile Phe Val Phe Val Ala Leu Ile Leu Ala Ile
1               5                   10                  15

Ser Ile Gly Gln Ser Glu Ala Gly Trp Leu Lys Lys Leu Gly Lys Arg
            20                  25                  30

Ile Glu Arg Ile Gly Gln His Thr Arg Asp Ala Thr Ile Gln Gly Leu
        35                  40                  45

Gly Ile Ala Gln Gln Ala Ala Asn Val Ala Ala Thr Ala Arg Gly
    50                  55                  60

<210> SEQ ID NO 25
<211> LENGTH: 31
<212> TYPE: PRT
<213> ORGANISM: Artificial Sequence
<220> FEATURE:
<223> OTHER INFORMATION: A synthetic peptide

<400> SEQUENCE: 25

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 26
<211> LENGTH: 13
<212> TYPE: PRT
<213> ORGANISM: Artificial Sequence
<220> FEATURE:
<223> OTHER INFORMATION: A synthetic peptide

<400> SEQUENCE: 26

Ile Leu Pro Trp Lys Trp Pro Trp Trp Pro Trp Arg Arg
1               5                   10

<210> SEQ ID NO 27
<211> LENGTH: 34
<212> TYPE: PRT
<213> ORGANISM: Artificial Sequence
<220> FEATURE:
<223> OTHER INFORMATION: A synthetic peptide

<400> SEQUENCE: 27

Ile Thr Ser Ile Ser Leu Cys Thr Pro Gly Cys Lys Thr Gly Ala Leu
```

```
                1               5                  10                  15
Met Gly Cys Asn Met Lys Thr Ala Thr Cys His Cys Ser Ile His Val
                20                      25                  30
Ser Lys

<210> SEQ ID NO 28
<211> LENGTH: 20
<212> TYPE: PRT
<213> ORGANISM: Artificial Sequence
<220> FEATURE:
<223> OTHER INFORMATION: A synthetic peptide

<400> SEQUENCE: 28

Phe Leu Gly Gly Leu Ile Lys Ile Val Pro Ala Met Ile Cys Ala Val
1               5                   10                  15
Thr Lys Lys Cys
            20

<210> SEQ ID NO 29
<211> LENGTH: 25
<212> TYPE: PRT
<213> ORGANISM: Artificial Sequence
<220> FEATURE:
<223> OTHER INFORMATION: A synthetic peptide

<400> SEQUENCE: 29

Phe Lys Cys Arg Arg Trp Gln Trp Arg Met Lys Lys Leu Gly Ala Pro
1               5                   10                  15
Ser Ile Thr Cys Val Arg Arg Ala Phe
            20                  25

<210> SEQ ID NO 30
<211> LENGTH: 19
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 19
<223> OTHER INFORMATION: Xaa = Any Amino Acid

<400> SEQUENCE: 30

Arg Gly Gly Arg Leu Cys Tyr Cys Arg Arg Arg Phe Cys Val Cys Val
1               5                   10                  15
Gly Arg Xaa

<210> SEQ ID NO 31
<211> LENGTH: 16
<212> TYPE: PRT
<213> ORGANISM: Artificial Sequence
<220> FEATURE:
<223> OTHER INFORMATION: A synthetic peptide

<400> SEQUENCE: 31

Gly Gly Arg Leu Cys Tyr Cys Arg Arg Arg Phe Cys Ile Cys Val Gly
1               5                   10                  15

<210> SEQ ID NO 32
<211> LENGTH: 51
<212> TYPE: PRT
<213> ORGANISM: Artificial Sequence
<220> FEATURE:
<223> OTHER INFORMATION: A synthetic peptide

<400> SEQUENCE: 32
```

Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
            35                  40                  45

Tyr Asp Asn
    50

<210> SEQ ID NO 33
<211> LENGTH: 38
<212> TYPE: PRT
<213> ORGANISM: Artificial Sequence
<220> FEATURE:
<223> OTHER INFORMATION: A synthetic peptide

<400> SEQUENCE: 33

Asp Ser His Glu Glu Arg His His Gly Arg His Gly His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
            35

<210> SEQ ID NO 34
<211> LENGTH: 33
<212> TYPE: PRT
<213> ORGANISM: Artificial Sequence
<220> FEATURE:
<223> OTHER INFORMATION: A synthetic peptide

<400> SEQUENCE: 34

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln

<210> SEQ ID NO 35
<211> LENGTH: 34
<212> TYPE: PRT
<213> ORGANISM: Artificial Sequence
<220> FEATURE:
<223> OTHER INFORMATION: A synthetic peptide

<400> SEQUENCE: 35

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 36
<211> LENGTH: 30
<212> TYPE: PRT
<213> ORGANISM: Artificial Sequence
<220> FEATURE:
<223> OTHER INFORMATION: A synthetic peptide

<400> SEQUENCE: 36

Ala Leu Trp Lys Asn Met Leu Lys Gly Ile Gly Lys Leu Ala Gly Lys
1               5                   10                  15

Ala Ala Leu Gly Ala Val Lys Lys Leu Val Gly Ala Glu Ser
            20                  25                  30

<210> SEQ ID NO 37
<211> LENGTH: 21
<212> TYPE: PRT
<213> ORGANISM: Artificial Sequence
<220> FEATURE:
<223> OTHER INFORMATION: A synthetic peptide

<400> SEQUENCE: 37

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 38
<211> LENGTH: 27
<212> TYPE: PRT
<213> ORGANISM: Artificial Sequence
<220> FEATURE:
<223> OTHER INFORMATION: A synthetic peptide

<400> SEQUENCE: 38

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 39
<211> LENGTH: 33
<212> TYPE: PRT
<213> ORGANISM: Artificial Sequence
<220> FEATURE:
<223> OTHER INFORMATION: A synthetic peptide

<400> SEQUENCE: 39

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Glu Gln
            20                  25                  30

Glu

<210> SEQ ID NO 40
<211> LENGTH: 33
<212> TYPE: PRT
<213> ORGANISM: Artificial Sequence
<220> FEATURE:
<223> OTHER INFORMATION: A synthetic peptide

<400> SEQUENCE: 40

Gly Phe Phe Ala Leu Ile Pro Lys Ile Ile Ser Ser Pro Ile Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 41
<211> LENGTH: 168
<212> TYPE: PRT
<213> ORGANISM: Artificial Sequence
<220> FEATURE:
<223> OTHER INFORMATION: A synthetic peptide -continued

```
<400> SEQUENCE: 41

Met Glu Thr Gln Arg Ala Ser Leu Ser Leu Gly Arg Cys Ser Leu Trp
 1               5                  10                  15

Leu Leu Leu Leu Gly Leu Val Leu Pro Ser Ala Gln Ala Leu Ser
             20                  25                  30

Tyr Arg Glu Ala Val Leu Arg Ala Val Asp Gln Phe Asn Glu Arg Ser
         35                  40                  45

Ser Glu Ala Asn Leu Tyr Leu Glu Leu Asp Pro Thr Pro Asn Asp Asp
 50                  55                  60

Leu Asp Pro Gly Thr Arg Lys Pro Val Ser Phe Arg Val Lys Glu Thr
 65                  70                  75                  80

Cys Pro Arg Thr Ser Gln Gln Pro Leu Glu Gln Cys Asp Phe Lys Glu
                 85                  90                  95

Asn Gly Leu Val Lys Gln Cys Val Gly Thr Thr Leu Asp Pro Ser Asn
                100                 105                 110

Asp Gln Phe Asp Ile Asn Cys Asn Glu Leu Gln Ser Val Arg Phe Arg
                115                 120                 125

Pro Pro Ile Arg Arg Pro Ile Arg Pro Pro Phe Tyr Pro Pro Phe Arg
            130                 135                 140

Pro Pro Ile Arg Pro Pro Ile Phe Pro Pro Ile Arg Pro Phe Arg Pro
145                 150                 155                 160

Pro Gly Pro Phe Pro Gly Arg Arg
                165

<210> SEQ ID NO 42
<211> LENGTH: 153
<212> TYPE: PRT
<213> ORGANISM: Artificial Sequence
<220> FEATURE:
<223> OTHER INFORMATION: A synthetic peptide

<400> SEQUENCE: 42

Met Glu Thr Pro Arg Ala Ser Leu Ser Leu Gly Arg Trp Ser Leu Trp
 1               5                  10                  15

Leu Leu Leu Leu Gly Leu Ala Leu Pro Ser Ala Ser Ala Gln Ala Leu
             20                  25                  30

Ser Tyr Arg Glu Ala Val Leu Arg Ala Val Asp Gln Leu Asn Glu Gln
         35                  40                  45

Ser Ser Glu Pro Asn Ile Tyr Arg Leu Leu Glu Leu Asp Gln Pro Pro
 50                  55                  60

Gln Asp Asp Glu Asp Pro Asp Ser Lys Arg Val Ser Phe Arg Val Lys
 65                  70                  75                  80

Glu Thr Val Cys Ser Arg Thr Thr Gln Gln Pro Pro Glu Gln Cys Asp
                 85                  90                  95

Phe Lys Glu Asn Gly Leu Leu Lys Arg Cys Glu Gly Thr Val Thr Leu
                100                 105                 110

Asp Gln Val Arg Gly Asn Phe Asp Ile Thr Cys Asn Asn His Gln Ser
            115                 120                 125

Ile Arg Ile Thr Lys Gln Pro Trp Ala Pro Pro Gln Ala Ala Arg Leu
        130                 135                 140

Cys Arg Ile Val Val Ile Arg Val Arg
145                 150

<210> SEQ ID NO 43
<211> LENGTH: 29
<212> TYPE: PRT
<213> ORGANISM: Artificial Sequence
```

```
<220> FEATURE:
<223> OTHER INFORMATION: A synthetic peptide

<400> SEQUENCE: 43

Ser Ile Gly Ser Ala Leu Lys Lys Ala Leu Pro Val Ala Lys Lys Ile
1               5                   10                  15

Gly Lys Ile Ala Leu Pro Ile Ala Lys Ala Ala Leu Pro
            20                  25

<210> SEQ ID NO 44
<211> LENGTH: 29
<212> TYPE: PRT
<213> ORGANISM: Artificial Sequence
<220> FEATURE:
<223> OTHER INFORMATION: A synthetic peptide

<400> SEQUENCE: 44

Ser Ile Gly Ser Ala Phe Lys Lys Ala Leu Pro Val Ala Lys Lys Ile
1               5                   10                  15

Gly Lys Ala Ala Leu Pro Ile Ala Lys Ala Ala Leu Pro
            20                  25

<210> SEQ ID NO 45
<211> LENGTH: 170
<212> TYPE: PRT
<213> ORGANISM: Artificial Sequence
<220> FEATURE:
<223> OTHER INFORMATION: A synthetic peptide

<400> SEQUENCE: 45

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170

<210> SEQ ID NO 46
<211> LENGTH: 170
<212> TYPE: PRT
<213> ORGANISM: Artificial Sequence
<220> FEATURE:
<223> OTHER INFORMATION: A synthetic peptide

<400> SEQUENCE: 46
```

-continued

Met Glu Thr Gln Arg Asn Thr Arg Cys Leu Gly Arg Trp Ser Pro Leu
1               5                   10                  15

Leu Leu Leu Leu Gly Leu Val Ile Pro Ala Thr Gln Ala Leu
            20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Lys Pro Val Ser Phe Met Val
65              70                  75                  80

Lys Glu Thr Val Cys Pro Arg Ile Met Lys Gln Thr Pro Glu Gln Cys
            85                  90                  95

Asp Phe Lys Glu Asn Gly Leu Val Lys Gln Cys Val Gly Thr Val Ile
            100                 105                 110

Leu Asp Pro Val Lys Asp Tyr Phe Asp Ala Ser Cys Asp Glu Pro Gln
            115                 120                 125

Arg Val Lys Arg Phe His Ser Val Gly Ser Leu Ile Gln Arg His Gln
        130                 135                 140

Gln Met Ile Arg Asp Lys Ser Glu Ala Thr Arg His Gly Ile Arg Ile
145                 150                 155                 160

Ile Thr Arg Pro Lys Leu Leu Leu Ala Ser
                165                 170

<210> SEQ ID NO 47
<211> LENGTH: 158
<212> TYPE: PRT
<213> ORGANISM: Artificial Sequence
<220> FEATURE:
<223> OTHER INFORMATION: A synthetic peptide

<400> SEQUENCE: 47

Met Glu Thr Gln Arg Ala Ser Leu Ser Leu Gly Arg Trp Ser Leu Trp
1               5                   10                  15

Leu Leu Leu Leu Gly Leu Ala Leu Pro Ser Ala Ser Ala Gln Ala Leu
            20                  25                  30

Ser Tyr Arg Glu Ala Val Leu Arg Ala Val Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Glu Asp Asp Glu Asn Pro Asn Pro Lys Pro Val Ser Phe Arg Val
65              70                  75                  80

Lys Glu Thr Val Cys Pro Arg Thr Ser Gln Gln Ser Pro Glu Gln Cys
            85                  90                  95

Asp Phe Lys Glu Asn Gly Leu Leu Lys Glu Cys Val Gly Thr Val Thr
            100                 105                 110

Leu Asp Gln Val Gly Ser Asn Phe Asp Ile Thr Cys Ala Val Pro Gln
            115                 120                 125

Ser Val Gly Gly Leu Arg Ser Leu Gly Arg Lys Ile Leu Arg Ala Trp
        130                 135                 140

Lys Lys Tyr Gly Pro Ile Ile Val Pro Ile Ile Arg Ile Gly
145                 150                 155

<210> SEQ ID NO 48
<211> LENGTH: 154
<212> TYPE: PRT
<213> ORGANISM: Artificial Sequence
<220> FEATURE:
<223> OTHER INFORMATION: A synthetic peptide

```
<400> SEQUENCE: 48

Met Glu Thr Gln Arg Asn Thr Arg Cys Leu Gly Arg Trp Ser Pro Leu
1               5                   10                  15

Leu Leu Leu Leu Gly Leu Val Ile Pro Pro Ala Thr Thr Gln Ala Leu
            20                  25                  30

Ser Tyr Lys Glu Ala Val Leu Arg Ala Val Asp Gly Leu Asn Gln Arg
        35                  40                  45

Ser Ser Asp Glu Asn Leu Tyr Arg Leu Leu Glu Leu Asp Pro Leu Pro
    50                  55                  60

Lys Gly Asp Lys Asp Ser Asp Thr Pro Pro Val Ser Phe Met Val Lys
65                  70                  75                  80

Glu Thr Val Cys Pro Arg Ile Met Lys Gln Thr Pro Glu Gln Cys Asp
                85                  90                  95

Phe Lys Glu Asn Gly Leu Val Lys Gln Cys Val Gly Thr Val Ile Leu
            100                 105                 110

Gly Pro Val Lys Asp His Phe Asp Val Ser Cys Gly Glu Pro Gln Arg
        115                 120                 125

Val Lys Arg Phe Gly Arg Leu Ala Lys Ser Phe Leu Arg Met Arg Ile
    130                 135                 140

Leu Leu Pro Arg Arg Lys Ile Leu Ala Ser
145                 150

<210> SEQ ID NO 49
<211> LENGTH: 159
<212> TYPE: PRT
<213> ORGANISM: Artificial Sequence
<220> FEATURE:
<223> OTHER INFORMATION: A synthetic peptide

<400> SEQUENCE: 49

Met Glu Thr Gln Arg Ala Ser Leu Ser Leu Gly Arg Cys Ser Leu Trp
1               5                   10                  15

Leu Leu Leu Leu Gly Leu Ala Leu Pro Ser Ala Ser Ala Gln Val Leu
            20                  25                  30

Ser Tyr Arg Glu Ala Val Leu Arg Ala Ala Asp Gln Leu Asn Glu Lys
        35                  40                  45

Ser Ser Glu Ala Asn Leu Tyr Arg Leu Leu Glu Leu Asp Pro Pro Pro
    50                  55                  60

Lys Gln Asp Asp Glu Asn Ser Asn Ile Lys Pro Val Ser Phe Arg Val
65                  70                  75                  80

Lys Glu Thr Val Cys Pro Arg Thr Ser Gln Gln Pro Ala Glu Gln Cys
                85                  90                  95

Asp Phe Lys Glu Asn Gly Leu Leu Lys Glu Cys Val Gly Thr Val Thr
            100                 105                 110

Leu Asp Gln Val Arg Asn Asn Phe Asp Ile Thr Cys Ala Glu Pro Gln
        115                 120                 125

Ser Val Arg Gly Leu Arg Arg Leu Gly Arg Lys Ile Ala His Gly Val
    130                 135                 140

Lys Lys Tyr Gly Pro Thr Val Leu Arg Ile Ile Arg Ile Ala Gly
145                 150                 155

<210> SEQ ID NO 50
<211> LENGTH: 12
<212> TYPE: PRT
<213> ORGANISM: Artificial Sequence
<220> FEATURE:
<223> OTHER INFORMATION: A synthetic peptide
```

<400> SEQUENCE: 50

Arg Leu Cys Arg Ile Val Val Ile Arg Val Cys Arg
1               5                   10

<210> SEQ ID NO 51
<211> LENGTH: 30
<212> TYPE: PRT
<213> ORGANISM: Artificial Sequence
<220> FEATURE:
<223> OTHER INFORMATION: A synthetic peptide

<400> SEQUENCE: 51

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 52
<211> LENGTH: 29
<212> TYPE: PRT
<213> ORGANISM: Artificial Sequence
<220> FEATURE:
<223> OTHER INFORMATION: A synthetic peptide

<400> SEQUENCE: 52

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 53
<211> LENGTH: 30
<212> TYPE: PRT
<213> ORGANISM: Artificial Sequence
<220> FEATURE:
<223> OTHER INFORMATION: A synthetic peptide

<400> SEQUENCE: 53

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 54
<211> LENGTH: 33
<212> TYPE: PRT
<213> ORGANISM: Artificial Sequence
<220> FEATURE:
<223> OTHER INFORMATION: A synthetic peptide

<400> SEQUENCE: 54

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 55
<211> LENGTH: 33
<212> TYPE: PRT
<213> ORGANISM: Artificial Sequence
<220> FEATURE:
<223> OTHER INFORMATION: A synthetic peptide

```
<400> SEQUENCE: 55

Val Val Cys Ala Cys Arg Arg Ala Leu Cys Leu Pro Arg Glu Arg
1               5                   10                  15

Ala Gly Phe Cys Arg Ile Arg Gly Arg Ile His Pro Leu Cys Cys Arg
            20                  25                  30

Arg

<210> SEQ ID NO 56
<211> LENGTH: 33
<212> TYPE: PRT
<213> ORGANISM: Artificial Sequence
<220> FEATURE:
<223> OTHER INFORMATION: A synthetic peptide

<400> SEQUENCE: 56

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 57
<211> LENGTH: 34
<212> TYPE: PRT
<213> ORGANISM: Artificial Sequence
<220> FEATURE:
<223> OTHER INFORMATION: A synthetic peptide

<400> SEQUENCE: 57

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 58
<211> LENGTH: 34
<212> TYPE: PRT
<213> ORGANISM: Artificial Sequence
<220> FEATURE:
<223> OTHER INFORMATION: A synthetic peptide

<400> SEQUENCE: 58

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg

<210> SEQ ID NO 59
<211> LENGTH: 34
<212> TYPE: PRT
<213> ORGANISM: Artificial Sequence
<220> FEATURE:
<223> OTHER INFORMATION: A synthetic peptide

<400> SEQUENCE: 59

Val Ser Cys Thr Cys Arg Arg Phe Ser Cys Gly Phe Gly Glu Arg Ala
1               5                   10                  15

Ser Gly Ser Cys Thr Val Asn Gly Gly Val Arg His Thr Leu Cys Cys
            20                  25                  30
```

Arg Arg

```
<210> SEQ ID NO 60
<211> LENGTH: 33
<212> TYPE: PRT
<213> ORGANISM: Artificial Sequence
<220> FEATURE:
<223> OTHER INFORMATION: A synthetic peptide

<400> SEQUENCE: 60

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 61
<211> LENGTH: 32
<212> TYPE: PRT
<213> ORGANISM: Artificial Sequence
<220> FEATURE:
<223> OTHER INFORMATION: A synthetic peptide

<400> SEQUENCE: 61

Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: A synthetic peptide

<400> SEQUENCE: 62

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: A synthetic peptide

<400> SEQUENCE: 63

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: A synthetic peptide

<400> SEQUENCE: 64

Arg Arg Cys Ile Cys Thr Thr Arg Thr Cys Arg Phe Pro Tyr Arg Arg
1               5                   10                  15
```

```
Leu Gly Thr Cys Ile Phe Gln Asn Arg Val Tyr Thr Phe Cys Cys
            20                  25                  30
```

<210> SEQ ID NO 65
<211> LENGTH: 67
<212> TYPE: PRT
<213> ORGANISM: Artificial Sequence
<220> FEATURE:
<223> OTHER INFORMATION: A synthetic peptide

<400> SEQUENCE: 65

```
Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
            35                  40                  45

Glu Glu Gln Ile Gly Lys Cys Ser Thr Arg Gly Arg Lys Cys Cys Arg
        50                  55                  60

Arg Lys Lys
65
```

<210> SEQ ID NO 66
<211> LENGTH: 18
<212> TYPE: PRT
<213> ORGANISM: Artificial Sequence
<220> FEATURE:
<223> OTHER INFORMATION: A synthetic peptide

<400> SEQUENCE: 66

```
Arg Cys Ile Cys Thr Arg Gly Phe Cys Arg Cys Leu Cys Arg Arg Gly
1               5                   10                  15

Val Cys
```

<210> SEQ ID NO 67
<211> LENGTH: 78
<212> TYPE: PRT
<213> ORGANISM: Artificial Sequence
<220> FEATURE:
<223> OTHER INFORMATION: A synthetic peptide

<400> SEQUENCE: 67

```
Met Lys Ser Ser Met Lys Met Phe Ala Ala Leu Leu Leu Val Val Met
1               5                   10                  15

Cys Leu Leu Ala Asn Glu Met Gly Gly Pro Leu Val Val Glu Ala Arg
            20                  25                  30

Thr Cys Glu Ser Gln Ser His Lys Phe Lys Gly Thr Cys Leu Ser Asp
            35                  40                  45

Thr Asn Cys Ala Asn Val Cys His Ser Glu Arg Phe Ser Gly Gly Lys
        50                  55                  60

Cys Arg Gly Phe Arg Arg Arg Cys Phe Cys Thr Thr His Cys
65                  70                  75
```

<210> SEQ ID NO 68
<211> LENGTH: 78
<212> TYPE: PRT
<213> ORGANISM: Artificial Sequence
<220> FEATURE:
<223> OTHER INFORMATION: A synthetic peptide

<400> SEQUENCE: 68

```
Met Lys Ser Ser Met Lys Met Phe Ala Ala Leu Leu Leu Val Val Met
```

```
                1               5                  10                 15
Cys Leu Leu Ala Asn Glu Met Gly Gly Pro Leu Val Val Glu Ala Arg
            20                  25                 30

Thr Cys Glu Ser Gln Ser His Lys Phe Lys Gly Thr Cys Leu Ser Asp
            35                  40                 45

Thr Asn Cys Ala Asn Val Cys His Ser Glu Arg Phe Ser Gly Gly Lys
            50                  55                 60

Cys Arg Gly Phe Arg Arg Arg Cys Phe Cys Thr Thr His Cys
65                  70                  75

<210> SEQ ID NO 69
<211> LENGTH: 30
<212> TYPE: PRT
<213> ORGANISM: Artificial Sequence
<220> FEATURE:
<223> OTHER INFORMATION: A synthetic peptide

<400> SEQUENCE: 69

Ala Cys Tyr Cys Arg Ile Pro Ala Cys Leu Ala Gly Glu Arg Arg Tyr
1               5                   10                  15

Gly Thr Cys Phe Tyr Met Gly Arg Val Trp Ala Phe Cys Cys
            20                  25                  30

<210> SEQ ID NO 70
<211> LENGTH: 37
<212> TYPE: PRT
<213> ORGANISM: Artificial Sequence
<220> FEATURE:
<223> OTHER INFORMATION: A synthetic peptide

<400> SEQUENCE: 70

Gly Phe Gly Cys Pro Phe Asn Gln Gly Ala Cys His Arg His Cys Arg
1               5                   10                  15

Ser Ile Arg Arg Arg Gly Gly Tyr Cys Ala Gly Leu Phe Lys Gln Thr
            20                  25                  30

Cys Thr Cys Tyr Arg
        35

<210> SEQ ID NO 71
<211> LENGTH: 38
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 28
<223> OTHER INFORMATION: Xaa = Any Amino Acid

<400> SEQUENCE: 71

Gly Phe Gly Cys Pro Asn Asn Tyr Gln Cys His Arg His Cys Lys Ser
1               5                   10                  15

Ile Pro Gly Arg Cys Gly Gly Tyr Cys Gly Gly Xaa His Arg Leu Arg
            20                  25                  30

Cys Thr Cys Tyr Arg Cys
        35

<210> SEQ ID NO 72
<211> LENGTH: 54
<212> TYPE: PRT
<213> ORGANISM: Artificial Sequence
<220> FEATURE:
<223> OTHER INFORMATION: A synthetic peptide
```

```
<400> SEQUENCE: 72

Asp Gly Val Lys Leu Cys Asp Val Pro Ser Gly Thr Trp Ser Gly His
 1               5                  10                  15

Cys Gly Ser Ser Lys Cys Ser Gln Gln Cys Lys Asp Arg Glu His
                20                  25                  30

Phe Ala Tyr Gly Gly Ala Cys His Tyr Gln Phe Pro Ser Val Lys Cys
            35                  40                  45

Phe Cys Lys Arg Gln Cys
        50

<210> SEQ ID NO 73
<211> LENGTH: 49
<212> TYPE: PRT
<213> ORGANISM: Artificial Sequence
<220> FEATURE:
<223> OTHER INFORMATION: A synthetic peptide

<400> SEQUENCE: 73

Asn Leu Cys Glu Arg Ala Ser Leu Thr Trp Thr Gly Asn Cys Gly Asn
 1               5                  10                  15

Thr Gly His Cys Asp Thr Gln Cys Arg Asn Trp Glu Ser Ala Lys His
                20                  25                  30

Gly Ala Cys His Lys Arg Gly Asn Trp Lys Cys Phe Cys Tyr Phe Asn
            35                  40                  45

Cys

<210> SEQ ID NO 74
<211> LENGTH: 90
<212> TYPE: PRT
<213> ORGANISM: Artificial Sequence
<220> FEATURE:
<223> OTHER INFORMATION: A synthetic peptide

<400> SEQUENCE: 74

Met Lys Lys Leu Val Leu Leu Phe Ala Leu Val Leu Leu Ala Phe Gln
 1               5                  10                  15

Val Gln Ala Asp Ser Ile Gln Asn Thr Asp Glu Glu Thr Lys Thr Glu
                20                  25                  30

Glu Gln Pro Gly Glu Lys Asp Gln Ala Val Ser Val Ser Phe Gly Asp
            35                  40                  45

Pro Gln Gly Ser Ala Leu Gln Asp Ala Ala Leu Gly Trp Gly Arg Arg
        50                  55                  60

Cys Pro Gln Cys Pro Cys Pro Ser Cys Pro Ser Cys Pro Arg Cys Pro
65                  70                  75                  80

Arg Cys Pro Arg Cys Lys Cys Asn Pro Lys
                85                  90

<210> SEQ ID NO 75
<211> LENGTH: 40
<212> TYPE: PRT
<213> ORGANISM: Artificial Sequence
<220> FEATURE:
<223> OTHER INFORMATION: A synthetic peptide

<400> SEQUENCE: 75

Gln Gly Val Arg Asn Phe Val Thr Cys Arg Ile Asn Arg Gly Phe Cys
 1               5                  10                  15

Val Pro Ile Arg Cys Pro Gly His Arg Arg Gln Ile Gly Thr Cys Leu
                20                  25                  30

Gly Pro Gln Ile Lys Cys Cys Arg
            35                  40
```

<210> SEQ ID NO 76
<211> LENGTH: 40
<212> TYPE: PRT
<213> ORGANISM: Artificial Sequence
<220> FEATURE:
<223> OTHER INFORMATION: A synthetic peptide

<400> SEQUENCE: 76

Gln Gly Val Arg Asn Phe Val Thr Cys Arg Ile Asn Arg Gly Phe Cys
1               5                   10                  15

Val Pro Ile Arg Cys Pro Gly His Arg Arg Gln Ile Gly Thr Cys Leu
            20                  25                  30

Gly Pro Arg Ile Lys Cys Cys Arg
        35                  40

<210> SEQ ID NO 77
<211> LENGTH: 42
<212> TYPE: PRT
<213> ORGANISM: Artificial Sequence
<220> FEATURE:
<223> OTHER INFORMATION: A synthetic peptide

<400> SEQUENCE: 77

Gln Gly Val Arg Asn His Val Thr Cys Arg Ile Tyr Gly Gly Phe Cys
1               5                   10                  15

Val Pro Ile Arg Cys Pro Gly Arg Thr Arg Gln Ile Gly Thr Cys Phe
            20                  25                  30

Gly Arg Pro Val Lys Cys Cys Arg Arg Trp
        35                  40

<210> SEQ ID NO 78
<211> LENGTH: 39
<212> TYPE: PRT
<213> ORGANISM: Artificial Sequence
<220> FEATURE:
<223> OTHER INFORMATION: A synthetic peptide

<400> SEQUENCE: 78

Gln Val Val Arg Asn Pro Gln Ser Cys Arg Trp Asn Met Gly Val Cys
1               5                   10                  15

Ile Pro Ile Ser Cys Pro Gly Asn Met Arg Gln Ile Gly Thr Cys Phe
            20                  25                  30

Gly Pro Arg Val Pro Cys Cys
        35

<210> SEQ ID NO 79
<211> LENGTH: 40
<212> TYPE: PRT
<213> ORGANISM: Artificial Sequence
<220> FEATURE:
<223> OTHER INFORMATION: A synthetic peptide

<400> SEQUENCE: 79

Gln Arg Val Arg Asn Pro Gln Ser Cys Arg Trp Asn Met Gly Val Cys
1               5                   10                  15

Ile Pro Phe Leu Cys Arg Val Gly Met Arg Gln Ile Gly Thr Cys Phe
            20                  25                  30

Gly Pro Arg Val Pro Cys Cys Arg
        35                  40

<210> SEQ ID NO 80

```
<211> LENGTH: 42
<212> TYPE: PRT
<213> ORGANISM: Artificial Sequence
<220> FEATURE:
<223> OTHER INFORMATION: A synthetic peptide

<400> SEQUENCE: 80

Gln Gly Val Arg Asn His Val Thr Cys Arg Ile Asn Arg Gly Phe Cys
1               5                   10                  15

Val Pro Ile Arg Cys Pro Gly Arg Thr Arg Gln Ile Gly Thr Cys Phe
            20                  25                  30

Gly Pro Arg Ile Lys Cys Cys Arg Ser Trp
        35                  40

<210> SEQ ID NO 81
<211> LENGTH: 40
<212> TYPE: PRT
<213> ORGANISM: Artificial Sequence
<220> FEATURE:
<223> OTHER INFORMATION: A synthetic peptide

<400> SEQUENCE: 81

Gln Gly Val Arg Ser Tyr Leu Ser Cys Trp Gly Asn Arg Gly Ile Cys
1               5                   10                  15

Leu Leu Asn Arg Cys Pro Gly Arg Met Arg Gln Ile Gly Thr Cys Leu
            20                  25                  30

Ala Pro Arg Val Lys Cys Cys Arg
        35                  40

<210> SEQ ID NO 82
<211> LENGTH: 41
<212> TYPE: PRT
<213> ORGANISM: Artificial Sequence
<220> FEATURE:
<223> OTHER INFORMATION: A synthetic peptide

<400> SEQUENCE: 82

Ser Gly Ile Ser Gly Pro Leu Ser Cys Gly Arg Asn Gly Gly Val Cys
1               5                   10                  15

Ile Pro Ile Arg Cys Pro Val Pro Met Arg Gln Ile Gly Thr Cys Phe
            20                  25                  30

Gly Arg Pro Val Lys Cys Cys Arg Ser
        35                  40

<210> SEQ ID NO 83
<211> LENGTH: 38
<212> TYPE: PRT
<213> ORGANISM: Artificial Sequence
<220> FEATURE:
<223> OTHER INFORMATION: A synthetic peptide

<400> SEQUENCE: 83

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 84
<211> LENGTH: 73
<212> TYPE: PRT
<213> ORGANISM: Artificial Sequence
<220> FEATURE:
```

-continued

<223> OTHER INFORMATION: A synthetic peptide

<400> SEQUENCE: 84

Ser Leu Gln Gly Gly Ala Pro Asn Phe Pro Gln Pro Ser Gln Gln Asn
1               5                   10                  15

Gly Gly Trp Gln Val Ser Pro Asp Leu Gly Arg Asp Asp Lys Gly Asn
            20                  25                  30

Thr Arg Gly Gln Ile Glu Ile Gln Asn Lys Gly Lys Asp His Asp Phe
        35                  40                  45

Asn Ala Gly Trp Gly Lys Val Ile Arg Gly Pro Asn Lys Ala Lys Pro
    50                  55                  60

Thr His Val Gly Gly Thr Tyr Arg Arg
65                  70

<210> SEQ ID NO 85
<211> LENGTH: 67
<212> TYPE: PRT
<213> ORGANISM: Artificial Sequence
<220> FEATURE:
<223> OTHER INFORMATION: A synthetic peptide

<400> SEQUENCE: 85

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 86
<211> LENGTH: 40
<212> TYPE: PRT
<213> ORGANISM: Artificial Sequence
<220> FEATURE:
<223> OTHER INFORMATION: A synthetic peptide

<400> SEQUENCE: 86

Ala Thr Cys Asp Leu Leu Ser Gly Phe Gly Val Gly Asp Ser Ala Cys
1               5                   10                  15

Ala Ala His Cys Ile Ala Arg Gly Asn Arg Gly Gly Tyr Cys Asn Ser
            20                  25                  30

Lys Lys Val Cys Val Cys Arg Asn
        35                  40

<210> SEQ ID NO 87
<211> LENGTH: 35
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 28
<223> OTHER INFORMATION: Xaa = Any Amino Acid

<400> SEQUENCE: 87

Gly Phe Gly Cys Pro Asn Asp Tyr Pro Cys His Arg His Cys Lys Ser
1               5                   10                  15

```
Ile Pro Gly Arg Tyr Gly Gly Tyr Cys Gly Gly Xaa His Arg Leu Arg
            20                  25                  30

Cys Thr Cys
        35
```

<210> SEQ ID NO 88
<211> LENGTH: 40
<212> TYPE: PRT
<213> ORGANISM: Artificial Sequence
<220> FEATURE:
<223> OTHER INFORMATION: A synthetic peptide

<400> SEQUENCE: 88

```
Ala Thr Cys Asp Leu Leu Ser Gly Ile Gly Val Gln His Ser Ala Cys
1               5                   10                  15

Ala Leu His Cys Val Phe Arg Gly Asn Arg Gly Gly Tyr Cys Thr Gly
            20                  25                  30

Lys Gly Ile Cys Val Cys Arg Asn
        35                  40
```

<210> SEQ ID NO 89
<211> LENGTH: 94
<212> TYPE: PRT
<213> ORGANISM: Artificial Sequence
<220> FEATURE:
<223> OTHER INFORMATION: A synthetic peptide

<400> SEQUENCE: 89

```
Met Arg Thr Leu Ala Leu Leu Ala Ala Ile Leu Leu Val Ala Leu Gln
1               5                   10                  15

Ala Gln Ala Glu His Val Ser Val Ser Ile Asp Glu Val Val Asp Gln
            20                  25                  30

Gln Pro Pro Gln Ala Glu Asp Gln Asp Val Ala Ile Tyr Val Lys Glu
        35                  40                  45

His Glu Ser Ser Ala Leu Glu Ala Leu Gly Val Lys Ala Gly Val Val
    50                  55                  60

Cys Ala Cys Arg Arg Ala Cys Leu Pro Arg Glu Arg Arg Ala Gly Phe
65                  70                  75                  80

Cys Arg Ile Arg Gly Arg Ile His Pro Leu Cys Cys Arg Arg
                85                  90
```

<210> SEQ ID NO 90
<211> LENGTH: 92
<212> TYPE: PRT
<213> ORGANISM: Artificial Sequence
<220> FEATURE:
<223> OTHER INFORMATION: A synthetic peptide

<400> SEQUENCE: 90

```
Met Lys Pro Leu Val Leu Leu Ser Ala Leu Val Leu Leu Ser Phe Gln
1               5                   10                  15

Val Gln Ala Asp Pro Ile Gln Asn Thr Asp Glu Glu Thr Lys Thr Glu
            20                  25                  30

Glu Gln Ser Gly Glu Asp Gln Ala Val Ser Val Ser Phe Gly Asp
        35                  40                  45

Arg Glu Gly Ala Ser Leu Gln Glu Glu Ser Leu Arg Asp Leu Val Cys
    50                  55                  60

Tyr Cys Arg Thr Arg Gly Cys Lys Arg Arg Glu Arg Met Asn Gly Thr
65                  70                  75                  80

Cys Arg Lys Gly His Leu Met Tyr Thr Leu Cys Cys
                85                  90
```

```
<210> SEQ ID NO 91
<211> LENGTH: 93
<212> TYPE: PRT
<213> ORGANISM: Artificial Sequence
<220> FEATURE:
<223> OTHER INFORMATION: A synthetic peptide

<400> SEQUENCE: 91

Met Lys Thr Phe Val Leu Leu Ser Ala Leu Val Leu Leu Ala Phe Gln
 1               5                  10                  15

Val Gln Ala Asp Pro Ile His Lys Thr Asp Glu Glu Thr Asn Thr Glu
            20                  25                  30

Glu Gln Pro Gly Glu Glu Asp Gln Ala Val Ser Ile Ser Phe Gly Gly
        35                  40                  45

Gln Glu Gly Ser Ala Leu His Glu Glu Leu Ser Lys Lys Leu Ile Cys
    50                  55                  60

Tyr Cys Arg Ile Arg Gly Cys Lys Arg Arg Glu Arg Val Phe Gly Thr
65                  70                  75                  80

Cys Arg Asn Leu Phe Leu Thr Phe Val Phe Cys Cys Ser
                85                  90

<210> SEQ ID NO 92
<211> LENGTH: 35
<212> TYPE: PRT
<213> ORGANISM: Artificial Sequence
<220> FEATURE:
<223> OTHER INFORMATION: A synthetic peptide

<400> SEQUENCE: 92

Leu Arg Asp Leu Val Cys Tyr Cys Arg Ala Arg Gly Cys Lys Gly Arg
 1               5                  10                  15

Glu Arg Met Asn Gly Thr Cys Arg Lys Gly His Leu Leu Tyr Met Leu
            20                  25                  30

Cys Cys Arg
        35

<210> SEQ ID NO 93
<211> LENGTH: 43
<212> TYPE: PRT
<213> ORGANISM: Artificial Sequence
<220> FEATURE:
<223> OTHER INFORMATION: A synthetic peptide

<400> SEQUENCE: 93

Ala Thr Cys Asp Ile Leu Ser Phe Gln Ser Gln Trp Val Thr Pro Asn
 1               5                  10                  15

His Ala Gly Cys Ala Leu His Cys Val Ile Lys Gly Tyr Lys Gly Gly
            20                  25                  30

Gln Cys Lys Ile Thr Val Cys His Cys Arg Arg
        35                  40

<210> SEQ ID NO 94
<211> LENGTH: 32
<212> TYPE: PRT
<213> ORGANISM: Artificial Sequence
<220> FEATURE:
<223> OTHER INFORMATION: A synthetic peptide

<400> SEQUENCE: 94

Val Thr Cys Tyr Cys Arg Ser Thr Arg Cys Gly Phe Arg Glu Arg Leu
 1               5                  10                  15
```

```
Ser Gly Ala Cys Gly Tyr Arg Gly Arg Ile Tyr Arg Leu Cys Cys Arg
            20                  25                  30
```

<210> SEQ ID NO 95
<211> LENGTH: 31
<212> TYPE: PRT
<213> ORGANISM: Artificial Sequence
<220> FEATURE:
<223> OTHER INFORMATION: A synthetic peptide

<400> SEQUENCE: 95

```
Val Thr Cys Ser Cys Arg Thr Ser Ser Cys Arg Phe Gly Glu Arg Leu
1               5                   10                  15

Ser Gly Ala Cys Arg Leu Asn Gly Arg Ile Tyr Arg Leu Cys Cys
            20                  25                  30
```

<210> SEQ ID NO 96
<211> LENGTH: 34
<212> TYPE: PRT
<213> ORGANISM: Artificial Sequence
<220> FEATURE:
<223> OTHER INFORMATION: A synthetic peptide

<400> SEQUENCE: 96

```
Gly Ile Cys Ala Cys Arg Arg Arg Phe Cys Leu Asn Phe Glu Gln Phe
1               5                   10                  15

Ser Gly Tyr Cys Arg Val Asn Gly Ala Arg Tyr Val Arg Cys Cys Ser
            20                  25                  30

Arg Arg
```

<210> SEQ ID NO 97
<211> LENGTH: 64
<212> TYPE: PRT
<213> ORGANISM: Artificial Sequence
<220> FEATURE:
<223> OTHER INFORMATION: A synthetic peptide

<400> SEQUENCE: 97

```
Met Arg Val Leu Tyr Leu Leu Phe Ser Phe Leu Phe Ile Phe Leu Met
1               5                   10                  15

Pro Leu Pro Gly Val Phe Gly Gly Ile Ser Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 98
<211> LENGTH: 64
<212> TYPE: PRT
<213> ORGANISM: Artificial Sequence
<220> FEATURE:
<223> OTHER INFORMATION: A synthetic peptide

<400> SEQUENCE: 98

```
Met Arg Val Leu Tyr Leu Leu Phe Ser Phe Leu Phe Ile Phe Leu Met
1               5                   10                  15

Pro Leu Pro Gly Val Phe Gly Gly Ile Gly Asp Pro Val Thr Cys Leu
            20                  25                  30

Lys Ser Gly Ala Ile Cys His Pro Val Phe Cys Pro Arg Arg Tyr Lys
        35                  40                  45

Gln Ile Gly Thr Cys Gly Leu Pro Gly Thr Lys Cys Cys Lys Lys Pro
    50                  55                  60
```

<210> SEQ ID NO 99
<211> LENGTH: 68
<212> TYPE: PRT
<213> ORGANISM: Artificial Sequence
<220> FEATURE:
<223> OTHER INFORMATION: A synthetic peptide

<400> SEQUENCE: 99

Met Arg Thr Ser Tyr Leu Leu Leu Phe Thr Leu Cys Leu Leu Leu Ser
1               5                   10                  15

Glu Met Ala Ser Gly Gly Asn Phe Leu Thr Gly Leu Gly His Arg Ser
            20                  25                  30

Asp His Tyr Asn Cys Val Ser Ser Gly Gly Gln Cys Leu Tyr Ser Ala
        35                  40                  45

Cys Pro Ile Phe Thr Lys Ile Gln Gly Thr Cys Tyr Arg Gly Lys Ala
    50                  55                  60

Lys Cys Cys Lys
65

<210> SEQ ID NO 100
<211> LENGTH: 64
<212> TYPE: PRT
<213> ORGANISM: Artificial Sequence
<220> FEATURE:
<223> OTHER INFORMATION: A synthetic peptide

<400> SEQUENCE: 100

Met Arg Leu His His Leu Leu Leu Val Leu Phe Phe Leu Val Leu Ser
1               5                   10                  15

Ala Gly Ser Gly Phe Thr Gln Gly Ile Arg Ser Arg Arg Ser Cys His
            20                  25                  30

Arg Asn Lys Gly Val Cys Ala Leu Thr Arg Cys Pro Arg Asn Met Arg
        35                  40                  45

Gln Ile Gly Thr Cys Phe Gly Pro Pro Val Lys Cys Cys Arg Lys Lys
    50                  55                  60

<210> SEQ ID NO 101
<211> LENGTH: 64
<212> TYPE: PRT
<213> ORGANISM: Artificial Sequence
<220> FEATURE:
<223> OTHER INFORMATION: A synthetic peptide

<400> SEQUENCE: 101

Met Arg Leu His His Leu Leu Leu Ala Leu Phe Phe Leu Val Leu Ser
1               5                   10                  15

Ala Gly Ser Gly Phe Thr Gln Gly Ile Ile Asn His Arg Ser Cys Tyr
            20                  25                  30

Arg Asn Lys Gly Val Cys Ala Pro Ala Arg Cys Pro Arg Asn Met Arg
        35                  40                  45

Gln Ile Gly Thr Cys His Gly Pro Pro Val Lys Cys Cys Arg Lys Lys
    50                  55                  60

<210> SEQ ID NO 102
<211> LENGTH: 95
<212> TYPE: PRT
<213> ORGANISM: Artificial Sequence
<220> FEATURE:
<223> OTHER INFORMATION: A synthetic peptide

<400> SEQUENCE: 102

Met Arg Thr Leu Val Ile Leu Ala Ala Ile Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Ser Leu Ala
            35                  40                  45

Trp Asp Glu Ser Leu Ala Pro Lys Asp Ser Val Pro Gly Leu Arg Lys
    50                  55                  60

Asn Met Ala Cys Tyr Cys Ile Pro Ala Cys Leu Ala Gly Glu Arg Arg
65                  70                  75                  80

Tyr Gly Thr Cys Phe Tyr Arg Arg Arg Val Trp Ala Phe Cys Cys
                85                  90                  95

<210> SEQ ID NO 103
<211> LENGTH: 96
<212> TYPE: PRT
<213> ORGANISM: Artificial Sequence
<220> FEATURE:
<223> OTHER INFORMATION: A synthetic peptide

<400> SEQUENCE: 103

Met Arg Thr Leu Val Ile Leu Ala Ala Ile Leu Val Ala Leu Gln
1               5                   10                  15

Ala Gln Ala Glu Pro Leu Gln Ala Arg Thr Asp Glu Ala Thr Ala Ala
            20                  25                  30

Gln Glu Gln Ile Pro Thr Asp Asn Pro Glu Val Val Ser Leu Ala
            35                  40                  45

Trp Asp Glu Ser Leu Ala Pro Lys Asp Ser Val Pro Gly Leu Arg Lys
    50                  55                  60

Asn Met Ala Cys Tyr Cys Arg Ile Pro Ala Cys Leu Ala Gly Glu Arg
65                  70                  75                  80

Arg Tyr Gly Thr Cys Phe Tyr Leu Gly Arg Val Trp Ala Phe Cys Cys
                85                  90                  95

<210> SEQ ID NO 104
<211> LENGTH: 33
<212> TYPE: PRT
<213> ORGANISM: Artificial Sequence
<220> FEATURE:
<223> OTHER INFORMATION: A synthetic peptide

<400> SEQUENCE: 104

Val Thr Cys Phe Cys Arg Arg Arg Gly Cys Ala Ser Arg Glu Arg His
1               5                   10                  15

Ile Gly Tyr Cys Arg Phe Gly Asn Thr Ile Tyr Arg Leu Cys Cys Arg
                20                  25                  30

Arg

<210> SEQ ID NO 105
<211> LENGTH: 31
<212> TYPE: PRT
<213> ORGANISM: Artificial Sequence
<220> FEATURE:
<223> OTHER INFORMATION: A synthetic peptide

<400> SEQUENCE: 105

Cys Phe Cys Lys Arg Pro Val Cys Asp Ser Gly Glu Thr Gln Ile Gly
1               5                   10                  15

Tyr Cys Arg Leu Gly Asn Thr Phe Tyr Arg Leu Cys Cys Arg Gln
                20                  25                  30

<210> SEQ ID NO 106
<211> LENGTH: 39
<212> TYPE: PRT
<213> ORGANISM: Artificial Sequence
<220> FEATURE:
<223> OTHER INFORMATION: A synthetic peptide

<400> SEQUENCE: 106

Gly Arg Lys Ser Asp Cys Phe Arg Lys Asn Gly Phe Cys Ala Phe Leu
1               5                   10                  15

Lys Cys Pro Tyr Leu Thr Leu Ile Ser Gly Lys Cys Ser Arg Phe His
            20                  25                  30

Leu Cys Cys Lys Arg Ile Trp
        35

<210> SEQ ID NO 107
<211> LENGTH: 43
<212> TYPE: PRT
<213> ORGANISM: Artificial Sequence
<220> FEATURE:
<223> OTHER INFORMATION: A synthetic peptide

<400> SEQUENCE: 107

Val Thr Cys Asp Leu Leu Ser Phe Glu Ala Lys Gly Phe Ala Ala Asn
1               5                   10                  15

His Ser Leu Cys Ala Ala His Cys Leu Ala Ile Gly Arg Arg Gly Gly
            20                  25                  30

Ser Cys Glu Arg Gly Val Cys Ile Cys Arg Arg
        35                  40

<210> SEQ ID NO 108
<211> LENGTH: 31
<212> TYPE: PRT
<213> ORGANISM: Artificial Sequence
<220> FEATURE:
<223> OTHER INFORMATION: A synthetic peptide

<400> SEQUENCE: 108

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: A synthetic peptide

<400> SEQUENCE: 109

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 110
<211> LENGTH: 29
<212> TYPE: PRT
<213> ORGANISM: Artificial Sequence
<220> FEATURE:
<223> OTHER INFORMATION: A synthetic peptide

<400> SEQUENCE: 110

Cys Tyr Cys Arg Ile Pro Ala Cys Ile Ala Gly Glu Arg Tyr Gly
1               5                   10                  15

Thr Cys Ile Tyr Gln Gly Arg Leu Trp Ala Phe Cys Cys
            20                  25

<210> SEQ ID NO 111
<211> LENGTH: 30
<212> TYPE: PRT
<213> ORGANISM: Artificial Sequence
<220> FEATURE:
<223> OTHER INFORMATION: A synthetic peptide

<400> SEQUENCE: 111

Asp Cys Tyr Cys Arg Ile Pro Ala Cys Ile Ala Gly Glu Arg Tyr
1               5                   10                  15

Gly Thr Cys Ile Tyr Gln Gly Arg Leu Trp Ala Phe Cys Cys
            20                  25                  30

<210> SEQ ID NO 112
<211> LENGTH: 33
<212> TYPE: PRT
<213> ORGANISM: Artificial Sequence
<220> FEATURE:
<223> OTHER INFORMATION: A synthetic peptide

<400> SEQUENCE: 112

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val

<210> SEQ ID NO 113
<211> LENGTH: 33
<212> TYPE: PRT
<213> ORGANISM: Artificial Sequence
<220> FEATURE:
<223> OTHER INFORMATION: A synthetic peptide

<400> SEQUENCE: 113

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 114
<211> LENGTH: 33
<212> TYPE: PRT
<213> ORGANISM: Artificial Sequence
<220> FEATURE:
<223> OTHER INFORMATION: A synthetic peptide

<400> SEQUENCE: 114

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 115
<211> LENGTH: 34
<212> TYPE: PRT

```
<213> ORGANISM: Artificial Sequence
<220> FEATURE:
<223> OTHER INFORMATION: A synthetic peptide

<400> SEQUENCE: 115

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 116
<211> LENGTH: 34
<212> TYPE: PRT
<213> ORGANISM: Artificial Sequence
<220> FEATURE:
<223> OTHER INFORMATION: A synthetic peptide

<400> SEQUENCE: 116

Gly Arg Cys Val Cys Arg Lys Gln Leu Leu Cys Ser Tyr Arg Glu Arg
1               5                   10                  15

Arg Ile Gly Asp Cys Lys Ile Arg Gly Val Arg Phe Pro Phe Cys Cys
            20                  25                  30

Pro Arg

<210> SEQ ID NO 117
<211> LENGTH: 33
<212> TYPE: PRT
<213> ORGANISM: Artificial Sequence
<220> FEATURE:
<223> OTHER INFORMATION: A synthetic peptide

<400> SEQUENCE: 117

Val Ser Cys Thr Cys Arg Arg Phe Ser Cys Gly Phe Gly Glu Arg Ala
1               5                   10                  15

Ser Gly Ser Cys Thr Val Asn Gly Val Arg His Thr Leu Cys Cys Arg
            20                  25                  30

Arg

<210> SEQ ID NO 118
<211> LENGTH: 33
<212> TYPE: PRT
<213> ORGANISM: Artificial Sequence
<220> FEATURE:
<223> OTHER INFORMATION: A synthetic peptide

<400> SEQUENCE: 118

Val Phe Cys Thr Cys Arg Gly Phe Leu Cys Gly Ser Gly Glu Arg Ala
1               5                   10                  15

Ser Gly Ser Cys Thr Ile Asn Gly Val Arg His Thr Leu Cys Cys Arg
            20                  25                  30

Arg

<210> SEQ ID NO 119
<211> LENGTH: 32
<212> TYPE: PRT
<213> ORGANISM: Artificial Sequence
<220> FEATURE:
<223> OTHER INFORMATION: A synthetic peptide

<400> SEQUENCE: 119

Val Thr Cys Tyr Cys Arg Arg Thr Arg Cys Gly Phe Arg Glu Arg Leu
1               5                   10                  15
```

Ser Gly Ala Cys Gly Tyr Arg Gly Arg Ile Tyr Arg Leu Cys Cys Arg
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: A synthetic peptide

<400> SEQUENCE: 120

Cys Ser Cys Arg Tyr Ser Ser Cys Arg Phe Gly Glu Arg Leu Leu Ser
1               5                   10                  15

Gly Ala Cys Arg Leu Asn Gly Arg Ile Tyr Arg Leu Cys Cys
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: A synthetic peptide

<400> SEQUENCE: 121

Ala Cys Thr Cys Arg Ile Gly Ala Cys Val Ser Gly Glu Arg Leu Thr
1               5                   10                  15

Gly Ala Cys Gly Leu Asn Gly Arg Ile Tyr Arg Leu Cys Cys Arg
            20                  25                  30

<210> SEQ ID NO 122
<211> LENGTH: 31
<212> TYPE: PRT
<213> ORGANISM: Artificial Sequence
<220> FEATURE:
<223> OTHER INFORMATION: A synthetic peptide

<400> SEQUENCE: 122

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 123
<211> LENGTH: 11
<212> TYPE: PRT
<213> ORGANISM: Artificial Sequence
<220> FEATURE:
<223> OTHER INFORMATION: A synthetic peptide

<400> SEQUENCE: 123

Arg Pro Lys Pro Gln Gln Phe Phe Gly Leu Met
1               5                   10

<210> SEQ ID NO 124
<211> LENGTH: 10
<212> TYPE: PRT
<213> ORGANISM: Artificial Sequence
<220> FEATURE:
<223> OTHER INFORMATION: A synthetic peptide

<400> SEQUENCE: 124

His Lys Thr Asp Ser Phe Val Gly Leu Met
1               5                   10

<210> SEQ ID NO 125

```
<211> LENGTH: 9
<212> TYPE: PRT
<213> ORGANISM: Artificial Sequence
<220> FEATURE:
<223> OTHER INFORMATION: A synthetic peptide

<400> SEQUENCE: 125

Asp Met His Asp Phe Val Gly Leu Met
1               5

<210> SEQ ID NO 126
<211> LENGTH: 19
<212> TYPE: PRT
<213> ORGANISM: Artificial Sequence
<220> FEATURE:
<223> OTHER INFORMATION: A synthetic peptide

<400> SEQUENCE: 126

Ala Gly His Gln Ile Ser His Lys Arg His Lys Thr Asp Ser Phe Val
1               5                   10                  15

Gly Leu Met

<210> SEQ ID NO 127
<211> LENGTH: 37
<212> TYPE: PRT
<213> ORGANISM: Artificial Sequence
<220> FEATURE:
<223> OTHER INFORMATION: A synthetic peptide

<400> SEQUENCE: 127

Asp Ala Asp Ser Ser Ile Glu Lys Gln Gln Val Ala Leu Leu Lys Ala
1               5                   10                  15

Leu Tyr Gly His Gly Gln Ile Ser His Lys Arg His Lys Thr Asp Ser
            20                  25                  30

Phe Val Gly Leu Met
        35

<210> SEQ ID NO 128
<211> LENGTH: 10
<212> TYPE: PRT
<213> ORGANISM: Artificial Sequence
<220> FEATURE:
<223> OTHER INFORMATION: A synthetic peptide

<400> SEQUENCE: 128

Gly Lys Ala Ser Gln Phe Phe Gly Leu Met
1               5                   10

<210> SEQ ID NO 129
<211> LENGTH: 14
<212> TYPE: PRT
<213> ORGANISM: Artificial Sequence
<220> FEATURE:
<223> OTHER INFORMATION: A synthetic peptide

<400> SEQUENCE: 129

Lys Lys Ala Tyr Gln Leu Glu His Thr Phe Gln Gly Leu Leu
1               5                   10

<210> SEQ ID NO 130
<211> LENGTH: 14
<212> TYPE: PRT
<213> ORGANISM: Artificial Sequence
<220> FEATURE:
<223> OTHER INFORMATION: A synthetic peptide

<400> SEQUENCE: 130
```

```
Val Gly Ala Tyr Gln Leu Glu His Thr Phe Gln Gly Leu Leu
 1               5                  10
```

COMPOSITION FOR COLD STORAGE OF STEM CELLS

BACKGROUND

Tens of thousands of transplants of marrow, peripheral blood stem cells and umbilical cord blood stem cells occur each year. Moreover, additional indications for transplantation of stem cell including hematopoietic stem cells continue to be reported, steadily increasing the number and frequency of transplants. The complexity of cell processing for transplantation also continues to grow and evolve rapidly, often resulting in longer processing times and necessitating transportation of cells to centers capable of performing more sophisticated cell processing procedures.

Hematopoietic cell transplantation may involve a donor and recipient treated at different institutions, e.g., allogenic transplantation. For autologous transplants, bone marrow is occasionally sent to a larger hospital for specialized treatment, such as the purging of tumor cells. Occasionally, cells to be transplanted are collected at one hospital, then transported to the transplant institution where the cells undergo processing and transplant. Due to geographic separation between donor and recipient, cells may be in transport for extended periods of time, e.g., 36 hours, and sometimes much longer between the cell harvest and arrival at the processing laboratory, as many donor programs match donor and recipients in different countries.

Following transport, cells can arrive at a processing laboratory at virtually any hour of the day or night, often with extensive processing still to be performed. The processing laboratory faces two alternatives: to store the cells until daytime staff are available, or to process the cells for transplantation immediately upon receipt. The latter requires 24-hour staffing for the processing laboratory and is clearly not possible at most institutions. The former alternative presents the problem of how to store the cells, in which bags, at what temperature and in which medium or solution. Clinical laboratories in general are neither staffed nor equipped to solve this problem to the satisfaction of transplant clinicians.

Since 1970, tissue culture medium has been used for the collection of transplantable hematopoietic stem cells (Thomas et al., *Blood*, 36:507 (1970)). Media designated for in vitro use, such as tissue culture medium, only contain combinations of inorganic salts, amino acids, vitamins, sugars, dyes, e.g., phenol red and other constituents not available in U.S.P. grade. These solutions employ a phosphate-based buffering system designed for use in the 5% $CO_2$ atmosphere of a cell culture incubator. Such a buffering system is, however, ineffective at atmospheric $CO_2$ concentrations. Cells stored and transported in these solutions are essentially without environmental pH control.

Because of the increasingly widespread use of bone marrow and peripheral blood progenitor cells in the treatment of malignancies and hematopoietic disorders, accrediting and regulatory agencies are developing and issuing standards and guidelines for the preparation of components for transplantation (Phillips et al., *Biol. of Blood and Marrow Transpln.*, 1:54 (1995); Standards for hematopoietic progenitor cell collection, processing and transplantation, Foundation for the Accreditation of Hematopoietic Cell Therapy ("FAHCT") 1st edn. (1996)). None of the tissue culture media used in marrow collection have been licensed by the United States Food and Drug Administration for in vivo human use. Other non-licensed agents such as dimethylsulfoxide ("DMSO") and Ficoll-hypaque are also used in the processing and preservation of stem cells and other hematopoietic cells but at this time there are no comparable approved substances with which to replace them.

There is a need for a medium for short-term storage of stem cells, e.g., prior to, during and after processing, that permits shipment of cells from a processing center to a transplant center in the absence of cryogenic conditions.

SUMMARY OF THE INVENTION

The invention provides a composition comprising cell maintenance or culture medium and a plurality of isolated factors ("trophic factors") for short term cold storage and preservation of therapeutic cells such as stem cells, e.g., non-adherent stem cells (i.e., those which may be maintained in suspension) or adherent stem cells, pluripotent cells or progenitor cells, prior to transplantation. In one embodiment, therapeutic cells are not terminally differentiated cells. In one embodiment, therapeutic cells are cells that can be maintained in suspension. The plurality of factors are selected from neurotrophins, such as brain derived nerve factor (BDNF) or nerve growth factor (NGF), polypeptide growth factors such as insulin-like growth factor (IGF) or epidermal growth factor (EGF), a neuropeptide such as Substance P, and antimicrobial peptides or membrane permeabilizing factors such as defensins or cathelicidins, and combinations thereof. In one embodiment, the composition does not include factors which promote differentiation of the cells. As used herein "short term storage" is storage for about 0.5 hour, e.g., at least 1 hour up to about 4 hours, and up to about 14 days, e.g., about 3 to about 7 days. As used herein "cold" storage is storage above freezing (0° C.) but less than 30° C., e.g., less than 25° C., e.g., storage from about 4° C. to about 10° C. In one embodiment, the therapeutic cell cold storage medium includes one or more neurotrophins, one or more neuropeptides, one or more IGF or IGF-like molecules, e.g., IGF-1 or EGF, and one or more antimicrobial peptides or membrane permeabilizing factors (e.g., defensins), in an amount effective to maintain therapeutic cell, e.g., stem cell, viability and function, as therapeutic cell integrity is an important factor in successful cell therapies, during storage and after transplant. Agents that protect cells from cold injury, e.g., agents that protect mitochondrial function, are anti-apoptotic, enhance cell viability, reduce the production of free radicals, protect cell function, decrease inflammation, alter MAP kinase kinetics, and/or activate Rac and Cdc42 GTPases, are useful in stem cell cold storage compositions of the invention. For instance, a therapeutic cell cold storage media of the invention may contain IGF (about 0.3 μg/mL to about 30 μg/mL or about 0.5 μg/mL to about 20 μg/L), NGF-beta (about 1 μg/mL to about 30 μg/L), bactenecin (e.g., BNP-1) (about 0.5 μg/mL to about 50 mg/L or about 1 μg/mL to about 10 mg/L) and Substance P (about 1 μg/mL to about 10 μg/mL, e.g., 2.5, mg/L).

Also provided are compositions comprising therapeutic cells such as stem cells, e.g., autologous, allogeneic or xenogenic cells, pluripotent cells or progenitor cells and a cell medium, for short term cold storage of those cells. In one embodiment, autologous cells may be harvested from a patient's bone marrow, adipose tissue or cardiac tissue, and may include mesenchymal stem cells (MSC), endothelial progenitor cells (EPC), smooth muscle cells (SMC), endothelial cells, or hematopoietic stem cells, or stem cells may be isolated from cord blood, e.g., isolated $CD34^+$ cells. The cells may be multipotent adult progenitor cells, side population stem cells, adult stem cells or embryonic stem cells. The composition of the invention also comprises a plurality of isolated factors selected from neurotrophins, neuropeptides, polypeptide growth factors, such as IGF, and an antimicrobial or membrane permeabilization factor such as a defensin or cathelicidin. For instance, a cell cold storage media of the invention may contain stem or progenitor cells and IGF-1 (about 1 μg/L to about 10 μg/L), NGF-beta (about 20 μg/L), bactenecin (about 1 mg/L) and Substance P (about 2.5 mg/L). The present invention is not limited to any particular base media or formulation so long as it is compatible with therapeutic cells such as stem cells, pluripotent cells or progenitor cells, i.e., does not adversely effect their viability or function. Indeed, a variety of medias and formulations are contemplated. For instance, the base media may be saline, X vivo-10, X vivo-15, or X vivo-20 with or without serum, e.g., 10% serum, NaCl+plasma, e.g., 2% plasma, RPE media (media conditioned by retinal pigment epithelia cells) with or without serum, HSC Gem/Stemline™ or StemSpan H2000™, or media generally employed to culture cells, such as DMEM with glucose, and without L-glutamine and sodium pyruvate. The cells may first be expanded prior to placement in the short term cold storage media. Alternatively, the cells may be expanded after transport in the short term cold storage media. In another embodiment, cells for transplant are harvested, placed in the short term cold storage media, and subsequently used in transplant without expansion.

Further provided are receptacles (containers) for cells, e.g., syringes, bags or tubes, and devices, having a plurality of the isolated trophic factors. In one embodiment, a receptacle may contain beads which elute, e.g., are coated or embedded with, the plurality of trophic factors. Further provided are implantable devices, e.g., a stent, vascular patch or myocardial patch having the plurality of factors. In one embodiment, the invention includes stents which elute the plurality of factors, e.g., during cell therapy in conjunction with stent placement. In one embodiment, the invention includes two- or three-dimensional matrices, e.g., vascular patch materials or valves, which elute the plurality of factors.

The media and devices of the present invention are not limited to any particular concentration of factors. Indeed, a range of concentrations are contemplated (e.g., from about 0.01 to 1000 mg/L and preferably from about 0.1 to 5 mg/L) for the factors of the invention, so long as the concentration of the factors provides for cell viability and maintenance of function, e.g., to proliferate, self-renew and/or differentiate. In one embodiment, the short term cold storage media of the invention provides for viabilities of at least 85%, e.g., 90% or more, such as 95%, after storage for about 7 days.

The therapeutic cells such as stem cells, pluripotent cells, or progenitor cells ("donor cells") in the cold storage media of the invention may be employed to treat myocardial infarction, stroke, heart failure, heart rhythm irregularities, diabetes, spinal cord injury and the like. Prior to implantation, the donor cells may be genetically engineered to express one or more of the trophic factors, e.g., inducible expression such as expression regulated by tetracycline or hypoxia, and in one embodiment, administered intravenously, intracardially or intermyocardially. In another embodiment, the trophic factors are delivered to the site of therapeutic cell transplant or delivered with an infusion of therapeutic cells.

BRIEF DESCRIPTION OF THE FIGURES

FIG. 3 is an illustration of an embodiment of a stent coated with trophic factors mounted on an expandable member of a catheter assembly.

FIG. 4 is an illustration of an embodiment of the stent and the expandable member in an expanded state.

FIG. 5 is an illustration of an embodiment of the stent with the expandable member removed.

DETAILED DESCRIPTION OF THE INVENTION

Definitions

Figure 1:
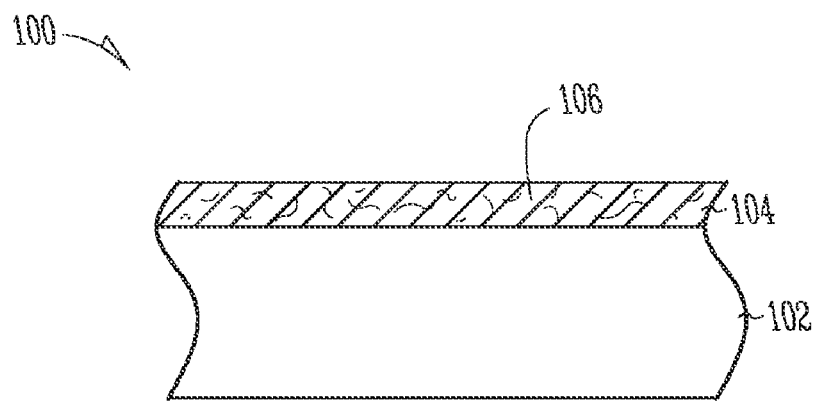
FIG. 1 is an illustration of an embodiment of an implantable device including a surface portion coated with trophic factors.

As used herein, the term "antimicrobial peptide" refers to peptides that inhibit the growth of microbes (e.g., bacteria). Examples of antimicrobial peptides include, but are not limited to, peptides described in Tables 2-4.

As used herein, the terms "neurotrophins", "neuropeptides" and "growth factors" refer to compounds that directly or indirectly bind to a cell surface receptor. Cell surface receptor binding compounds can be proteins (e.g., IGF-1, NGF-β, EGF and Substance P), either purified from natural sources or genetically engineered, as well as fragments thereof with substantially the same activity as the corresponding full length mature protein.

The term "isolated" when used in relation to a peptide, polypeptide, or cell, refers to a peptide, polypeptide, or cell that is identified and/or separated from at least one contaminant nucleic acid, polypeptide, cell type or other biological component with which it is ordinarily associated in its natural source. Isolated peptide, polypeptide, or stem cells are present in a form or setting that is different from that in which it is found in nature. "Purified" includes when an object species is the predominant species present (e.g., it is more abundant than any other individual species in the composition), and preferably the object species comprises at least about 50 percent of all macromolecular species present. Generally, "substantially purified" includes when an object species is more than about 80 percent of all macromolecular species present in a composition, e.g., more than about 85%, about 90%, about 95%, or about 99%.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

General Overview

The present invention relates to media and devices comprising antimicrobial or membrane permeabilizing peptides and cell surface receptor binding compounds, and their use for the storage and preservation of isolated donor cells prior to transplant. It is contemplated that the use of the media of the present invention to maintain donor cells prior to transplant results both in improved function of the cells after transplant and in an increase in the length of time the donor cells can be stored. Accordingly, improved compositions and devices for donor cell transplant are described in detail below.

In one embodiment, the invention provides cell therapy systems or kits (including storage media and delivery devices) having a plurality of isolated trophic factors. The systems or kits may include a biopacer (genetically modified cells that restore cardiac pacemaker function), acute myocardial infarction (AMI) treatments, AMI to heart failure (HF) treatments (device plus stem cell co-therapies), as well as those for cartilage regeneration and bone formation. In one embodiment, the plurality of trophic factors are applied to an implantable device, e.g., a stent, a vascular or myocardial patch, a bead or the inner surface of a storage container (receptacle) for cells, e.g., tubes or bags, or to a cell collection syringe. In another embodiment, stents having or progenitor cells applied thereto, e.g., cultured on the luminal surface, may be placed in cold storage media having the trophic factors. In one embodiment, the plurality of factors are introduced to the matrix of a stent or bead, to a patch or other 2- or 3-dimensional biocompatible structures, e.g., artificial skin products or other tissue replacement products derived from living cells attached to a substrate, or other biocompatible polymer. Beads with the trophic factors may be formed of any biocompatible material, e.g., biocompatible polymers, and introduced to a cell storage container or administered to a mammal subjected to, or in conjunction with, cell therapy. Biocompatible polymers include but are not limited to polyacrylamide, magnetic materials, alginate, agar, agarose, sepharose, a hydrogel, collagen, plastic, glass, polystyrene, latex, gold, dextran, hydroxyapetite, or Sephadex. Stents with the trophic factors may be formed of any biocompatible material and administered to a mammal subjected to, or in conjunction with, cell therapy.

Donor Cells, Isolation Thereof, and Cell Media

A cell population useful in the media and devices of the invention includes one which is capable of developing into cells of mesodermal cell lineage, ectodermal cell lineage and/or endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. In one embodiment, cells within a stem cell population for use in the present invention include cells of at least one of the following cellular lineages: hematopoietic cell lineage, endothelial cell lineage, epithelial cell lineage, muscle cell lineage and/or neural cell lineage or having the potential to differentiate into one or more of these lineages.

A stem cell must be capable of self-renewal, undergoing symmetric or asymmetric divisions through which the stem cell population is maintained. Symmetric division implies that both the daughter cells retain full stem cell characteristics, whereas asymmetric division refers to only one of the two daughter cells remains a stem cell while the other continues on a differentiation pathway. A single stem cell must be capable of multilineage differentiation. In other words, the ability to differentiate to multiple lineages must not be due to the presence of a mixture of cells having different differentiation. Finally, a stem cell must be capable of in vivo function reconstitution of a given tissue.

Embryonic stem (ES) cells have unlimited self-renewal and differentiation potential. They are capable of giving rise to cells of the three somatic germ layers that constitute an organism: mesoderm, ectoderm and endoderm, and so are pluripotent. ES cells are derived from the inner cell mass of blastocysts. Under specific culture conditions, ES cells differentiate into multicellular embryoid bodies containing differentiated cells from all three germ layers including cardiomyocytes. Human ES cell-derived cardiomyocytes display structural and functional properties of early-stage cardiomyocytes that couple electrically with host cardiomyocytes when transplanted into normal myocardium (Kehat et al., *J. Clin. Invest.*, 108:407 (2001); Kehat et al., *Nat. Biotechnol.*, 22:1282 (2004)). Nuclear transfer techniques provide a means for generating an unlimited supply of histocompatible ES cells for the treatment of cardiac disease (therapeutic cloning) (Lanza et al., *Circ. Res.*, 94:820 (2004)). Both mouse and hES cells were originally derived using MEF feeder layers and serum-containing medium (Martin, *Proc. Natl. Acad. Sci. USA*, 78:7634 (1981); Evans et al., *Nature*, 292:154 (1981); Thomson et al., *Science*, 282:1145 (1995)). For mouse ES cells, LIF can substitute for the feeder layer. Maintenance of hES cells can be accomplished on human feeders derived from fetal skin, fetal muscle, foreskin cells, adult skin fibroblasts and adult marrow cells. Moreover, derivation of new hES cell lines using human feeders derived from fetal muscle, fetal skin, adult fallopian tube epithelial cells and uterine endometrial cells has also been demonstrated (Richards et al., *Nat. Biotech.*, 20:933 (2002); Lee et al., *Biol. Reprod.*, 72:42 (2005); Horarta et al., *Hum. Reprod.*, 18:1404 (2003)).

Adult stem cells have a more restricted, self-renewal and differentiation potential is more restricted when compared to ES cells. Moreover, a population of pluripotent stem cells termed multipotent adult progenitor cells (MAPC) has been isolated from the bone marrow of post-natal human and rodents (Jiang et al., *Nature*, 418:41 (2002); Reyes et al., *Blood*, 98:2615 (2001); Reyes et al., *Ann. N.Y. Acad. Sci.*, 938:231 (2001)). These cells can be expanded in vitro without senescence, and provide clonal in vitro cells of the three germ lineages.

HSC can be obtained from bone marrow, peripheral blood and umbilical cord blood. The general protocol for isolating MSCs from bone marrow involves isolation of the mononuclear cells (usually by gradient centrifugation) and seeding these cells on tissue culture plates in medium containing fetal bovine serum (FBS). After attachment of the adherent cell fraction, the medium is removed to eliminate non-adherent cells.

EPCs were originally defined by their cell surface expression of the hematopoietic marker proteins CD133 and CD34 and the endothelial marker vascular endothelial growth factor receptor-2, and their capacity to incorporate into sites of neovascularization and to differentiate into endothelial cells in situ (Asahara, *Am. J. Physiol. Cell Physiol.*, 287:C572 (2004)). Increasing evidence suggests that culture-expanded EPCs also contain a $CD14^+/CD34^-$-mononuclear cell population with "EPC capacity," which mediates its angiogenic effects by releasing paracrine factors (Rehman et al., *Circulation*, 107:1165 (2003); Urbich et al., *Circ. Res.*, 95:343 (2004)).

The cell surface antigen CD133 is expressed on early HSCs and EPCs, both of which collaborate to promote vascularization of ischemic tissues (Rafii et al., *Nat. Med.*, 2:702 (2003)). Primitive hematopoietic progenitor cells (primarily CD133+ or CD34+) may be isolated from fresh, or frozen, hematopoietic tissue (cord blood (CB), bond marrow (BM) or growth factor-mobilized blood). A number of techniques are available to perform this isolation, including the Miltenyi MACS® system (Biotec, Inc., Auburn, Calif., USA) or the Baxter Isolex® device (Baxter Deerfiled, Ill., USA) and purities of greater than 90% CD133+ or CD34+ can be achieved. Isolated CD133+ or CD34+ cells are subsequently incubated in medium. $CD133^+$ cells can integrate into sites of neovascularization and differentiate into mature endothelial cells. Because CD133 expression is lost on myelomonocytic cells, this marker provides an effective means to distinguish "true" $CD133^+$ EPCs from EPCs of myelomonocytic origin (Rehman et al., supra). Less than 1% of nucleated BMCs are $CD133^+$, and because these cells cannot be expanded ex vivo, only limited numbers of $CD133^+$ cells can be obtained for therapeutic purposes.

MSCs represent a rare population of $CD34^-$ and $CD133^-$ cells present in bone marrow stroma (10-fold less abundant than HSCs) and other mesenchymal tissues (Pittenger et al., Circ. Res., 95:9 (2004)). Mesenchymal stem cells (MSC) can be isolated as plastic-adherent cells from a variety of fetal and adult tissues. Coculture of CB with MSC provides an alternative strategy to liquid CB expansion. One advantage of the HSC-MSC co-culture techniques is that no isolation of the CB HSC is required prior to expansion, minimizing sample manipulation and loss of HSC. Briefly, mononuclear cells (MNC) are isolated by density separation and cocultured with established MSC monolayers in medium containing FBS and a growth factor cocktail (e.g., SCF, TPO and G-GSF, as with liquid culture expansion) (McNiece et al., Cytotherapy, 6:311 (2004)). Non-adherent cells may be removed from the co-culture after 7 days and subsequently expanded using liquid culture protocol.

MSCs can readily differentiate into osteocytes, chondrocytes, and adipocytes. Differentiation of MSCs to cardiomyocyte-like cells has been observed under specific culture conditions and after injection into healthy or infarcted myocardium in animals (Makino et al., J. Clin. Invest., 103:697 (1999); Toma et al., Circulation, 105:93 (2002); Mangi et al., Nat. Med., 9:1195 (2003)). When injected into infarct tissue, MSCs may enhance regional wall motion and prevent remodeling of the remote, noninfarcted myocardium (Mangi et al., 2003; Shake et al., Ann. Thorac. Sur., 73:1919 (2002). Cultured MSCs secrete angiogenic cytokines, which improve collateral blood flow recovery in a murine hind limb ischemia model (Kinnaird et al., Circ. Res., 94:678 (2004)). Because MSC clones can be expanded in vitro, and reportedly have a low immunogenicity, they may be used in an allogeneic setting (Pittenger et al., Circ. Res., 95:9 (2004)).

Skeletal myoblasts, or satellite cells, are progenitor cells that normally lie in a quiescent state under the basal membrane of mature muscular fibers. Myoblasts can be isolated from skeletal muscle biopsies and expanded in vitro. Myoblasts differentiate into myotubes and retain skeletal muscle properties when transplanted into an infarct scar (Ghostine et al., Circulation, 106:1131 (2002); Murry et al., J. Clin. Invest., 98:2512 (1996); Leobon et al., Proc. Natl. Acad. Sci. USA, 100:7808 (2003); Pagani et al., J. Am. Coll. Cardiol., 41:879 (2003)). Myoblast transplantation has been shown to augment systolic and diastolic performance in animal models of myocardial infarction (Dowell et al., Cardiovasc. Res., 58:336 (2003)).

Resident cardiac stem cell (CSC) population(s) are capable of differentiating into cardiomyocyte or vascular lineages (Hierlihy et al., FEBS Lett., 530:239 (2002); Beltrami et al., Cell, 114:763 (2003); Oh et al., Proc. Natl. Acad. Sci. USA, 100:12313 (2003); Martin et al., Dev. Biol., 265:262 (2004); Messina et al., Circ. Res., 95:911 (2004)). Intriguingly, CSCs can be clonally expand from human myocardial biopsies (Messina et al., 2004). It has been reported that intramyocardial injection of these cells after AMI in mice promotes cardiomyocyte and vascular cell formation and leads to an improvement in systolic function (Messina et al., 2004).

Cloned stem cells are prepared using nuclear transfer, adult cells and embryos, and obtaining cells from a resulting blastocyst or a population of cells derived therefrom.

In one embodiment, stem cells and other cells, which may be stored in the media or receptacles of the invention, include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated $CD34^+$ cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. The term "donor cell" includes embryonic, fetal, pediatric, or adult cells or tissues, including but not limited to, stem cells and precursors (progenitor) cells. Thus, donor cells of the invention can be myocardial cells, bone marrow cells, hematopoietic cells, lymphocytes, leukocytes, granulocytes, hepatocytes, monocytes, macrophages, fibroblasts, neural cells, mesenchymal stem cells, beta-islet cells, and combinations thereof, or cells capable of differentiating into those cells. In one embodiment, the donor cells are autologous cells, however, non-autologous cells, e.g., xenogenic cells, may also be employed. In one embodiment, the donor cells are endothelial progenitor cells, $CD133^+$ cells, $CD34^+$ cells, mesenchymal stem cells, skeletal myoblasts, neural stem cells, pancreatic beta cells, cardiac stem cells or embryonic stem cells.

Stem cells may be isolated from any source known in the art and includes, but is not limited to, e.g., peripheral blood stem cells (PBSC), stem cells isolated from bone marrow; stem cells isolated from adipose tissue; mesenchymal stem cells, embryonic stem cells, $CD34^+$ cells, $CD34^-$ cells, $CD45^+$ cells, or combinations thereof). Stem cells which express one or more of the following antigens may be useful in the methods of the invention: CD34, CD133, ABCG2, Sca-1, Stro-1, nestin, PSA-NCAm, P75 neurotrophin, c-kit or CD30. Exemplary stem cells and methods of isolating them are described in, e.g., Fickert et al., Osteoarthritis Cartilage, 11:790 (2003), which discloses identification, quantification and isolation of human mesenchymal progenitor cells from osteoarthritic synovium; Meirelles et al., Br. J. Haematol., 123:702 (2003), which discloses isolation, in vitro expansion, and characterization of mesenchymal stem cell from bone marrow; Pittenger et al., Science, 284:143 (1999), which discloses isolation, analysis, and differentiation of adult human mesenchymal stem cells from bone marrow; Lataillade et al., Blood, 95:756 (2000) or Handgretinger et al., Bone Marrow Transplant, 27:777 (2001), which disclose isolation, analysis, and purification of adult human peripheral blood $CD34^+$ progenitor cells; U.S. Pat. No. 6,667,034 which discloses isolation and differentiation of stem cells from human hematopoietic cells, i.e., from bone marrow and peripheral blood; and U.S. Pat. No. 6,261,549 which discloses isolation of human mesenchymal stem cells from peripheral blood; and Gepstein, Circ. Res., 91:866 (2002), which discloses derivation of embryonic stem cells.

Typically, stem cells are purified from peripheral blood using methods known in the art including, e.g., immunomagnetic selection with the MACS system (Miltenyi Biotech, Tebu) or antibody-coated Dynabeads (Dynal Biotech, Oslo). A heterogeneous population of cells may be contacted with antibody-coated magnetic beads. The antibody specifically binds to a cell surface marker differentially or preferentially expressed on the surface of a stem cell, thereby forming a complex between the beads and the stem cells in the heterogeneous population. The labeled stem cells can then be isolated from the heterogeneous cell population using methods known in the art including, e.g., flow cytometry.

For example, bone marrow is aspirated from the posterior iliac crest under a brief general anesthesia. Unselected BMCs are enriched under good manufacturing practice conditions by 4% gelatin-polysuccinate density gradient sedimentation as described in Wollert et al. (*Lancet*, 364:141 (2004)). CD34$^+$ cells may be immunomagnetically enriched from unselected BMCs by the CliniMACS$^{plus}$ System and CD34 antibodies from Miltenyi Biotech. The number of CD34+ cells in unselected BMC preparations and in CD34-enriched preparations may be determined by flow cytometry analysis (FACSCalibur, BD Biosciences) using an antibody from Beckman Coulter.

Alternatively, BMCs are isolated by Ficoll density gradient centrifugation. After two washing steps, cells are resuspended to yield a heterogeneous cell population including hematopoietic progenitor cells, but also other cell types (e.g., side population cells, stromal cells, and so on). Overall, a mean value of 5.5±3.9×10$^6$ CD34/CD45-positive cells may be infused per patient.

For CPCs, mononuclear cells from venous blood are suspended in medium supplemented with 1 ng/ml carrier-free human recombinant vascular endothelial growth factor (R&D, Wiesbaden, Germany), 0.1 μmol/L atorvastatin (Pfizer, Freiburg, Germany), and 20% human serum drawn from each individual patient. Cells are seeded at a density of 6.4×10$^5$ cells/mm$^2$ on fibronectin-coated dishes (Roche, Grenzach, Germany). After three days of cultivation, cells are detached with 0.5 mmol/L ethylenediamine-tetraacetic acid, washed twice, and re-suspended in a final volume of 10 ml of medium. The resulting cell suspension contains a heterogeneous population of progenitor cells, however, more than 90% of the cells show endothelial characteristics, as demonstrated by Dil-acetylated low-density lipoprotein-uptake and lectin binding and the expression of typical endothelial marker proteins including vascular endothelial growth factor-R2 (KDR) (ReliaTech, Braunschweig, Germany), endoglin (CD105) (NeoMarkers, Asbach, Germany), von Willebrand factor (Oncogene, Schwalbach, Germany), and platelet endothelial cell adhesion molecule-1 (PECAM-1/CD31) (Dianova, Hamburg, Germany) (Assmus et al., *Circulation*, 106: 3009 (2002); Dimmeler et al., *J. Clin. Invest.*, 108:391 (2001); Vasa et al., *Circulation*, 103:2885 (2001); Vasa et al., *Circ. Res.*, 89:1 (2001)).

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells are removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

Media for stem cells has been described. See, e.g., U.S. Pat. Nos. 7,109,032, 7,101,710, 7,037,892, 6,787,353, 6,777,233, 6,642,048, 6,277,557, 6,162,643, 5,955,277, 5,908,782, 5,397,706, U.S. published application Nos. 20060084168, 2006014279, 20050244962, 20050233446, 20051142118 and 20040214319, Draper et al. (*Stem Cells & Devel.*, 13:325 (2004), Skottman et al., *FEBS Lett.*, 580:2875 (2006)), and Table 1. In one embodiment, the media is serum- or plasma-free. Base media for the cold storage media of the invention may be growth (expansion) media without serum, with serum, or only with the trophic factors.

TABLE 1

| Cell type | FBS | Growth factors |
|---|---|---|
| hES | None | bFGF 4-40 ng/ml |
| mES | 15% | LIF 1000 units/ml |
| hMAPC | 2% | EGF 10 ng/ml, PDGF 10 ng/ml |
| mMAPC | 2% | EGF 10 ng/ml, PDGF 10 ng/ml, LIF 1000 units/ml |
| hMSC | 10% | bFGF 1 ng/ml |
| hMSC STRO1+ | None | EGF 10 ng/ml, PDGF 10 ng/ml |
| hES | 20% | SCF 300 ng/ml, Flt-3 200 ng/ml, IL-3 10 ng/ml, IL-6 10 ng/ml, GCSF 50 ng/ml, BMP-4 50 ng/ml |
| hES | None | bFGF 20 ng/ml |
| mES | 15% | RA 10$^{-8}$ M, aFGF 100 ng/ml, FGF-4 20 ng/ml, HGF 50 ng/ml |
| mMAPC | None | bFGF 100 ng/ml, FGF-8 10 ng/ml, BDNF 10 ng/ml |
| hMAPC | None | VEGF-B 10 ng/ml |
| h m MAPC | None | FGF-4 10 ng/ml, HGF 10 ng/ml | h, Human;
m, mouse.

Serum in stem cell media generally has replaced FBS with Serum Replacer (GibcoBRL; Patent WO 98/30679, 1998) which still contains animal derived proteins. FBS concentrations for maintenance media can range from 0-20%, e.g., 2 to 15%. hES cell pluripotency may be maintained in media containing Serum Replacer and fibroblast growth factor 2 in the presence of MEF (Amit et al., *Dev. Biol.*, 227:271 (2000)). Moreover, TGF-β was found to promote maintenance of undifferentiated ES cells (James et al., *Development*, 132: 1273 (2005) and Amit et al., *Biol. Reprod.*, 70:837 (2004)). Nevertheless, there are reports that high concentrations of bFGF are needed to maintain hES cells in feeder free conditions (Wang et al., *Blood*, 105:4598 (2005) and Xu et al., *Nat. Methods*, 2:185 (2005)).

Serum-free preservation media such as the University of Wisconsin (UW) media may cause tissue damage through trophic factor (TF) deprivation. UW solution may be supplemented with IGF-I, nerve growth factor-β (NGF-β), bactenecin, and Substance P, to create a stem cell storage media that maintains stem cells during cold storage at 4° C.

Trophic Factors

The antimicrobials, neuropeptides, neurotrophins or polypeptide growth factors useful in the compositions and devices of the invention can be isolated and purified from natural sources as appropriate. The antimicrobials, neuropeptides, neurotrophins or polypeptide growth factors may also be produced recombinantly or synthetically. In some embodiments, the media or devices of the present invention comprise one or more antimicrobial peptides, neuropeptides, neurotrophins or polypeptide growth factors at a concentration of about 0.01 to 1000 mg/L. In some embodiments, the media comprises a solution comprising one or more antimicrobial peptides at a concentration of about 0.1 to 5 mg/L. In some embodiments, EGF, IGF-1, and/or NGF are included at a concentration of about 1 ng/ml to 100 ng/ml, e.g., about 10 ng/ml. In other embodiments, substance P is included at a concentration of about 0.1 µg/ml to 100 µg/ml, e.g., about 2.5 µg/ml.

Antimicrobial Peptides and Membrane Permeabilization Factors

The use of membrane permeabilization during ex vivo cold storage of donor cells is counterintuitive to the currently accepted precepts of preservation science, where membrane permeabilization is considered to be a hallmark of storage injury (Stefanovich et al., Cryobiology, 32:389 (1995)). Antimicrobial peptides such as defensins and cathelicidins, may permeabilize membrane.

Antimicrobial peptides comprise a diverse array of peptides that are apart of the innate immune system and found endogenously in many species, of which the defensins were first described. The antimicrobial peptides are small proteins (generally <100 amino acids), e.g., bactenecin has 12 amino acids and a single disulfide bridge (Koczulla et al., Drugs, 63:389 (2003); Martin et al., J. Leukoc. Biol., 58:128 (1995)). The antimicrobial peptides are best known for their broad spectrum of activity against microorganisms, an effect which is mediated in large part via lethal permeabilization of microbial cell membranes (Huang, Biochemistry, 39:8347 (2000); Kagan et al., Proc. Natl. Acad. Sci. USA, 87:210 (1990)). However, low concentrations of antimicrobial peptides have also been reported to have receptor-mediated activities including activation of cell signaling cascades, stimulation of eukaryotic gene transcription and various other cellular functions (Koczulla et al., 2003).

Differences in action of the various antimicrobial peptides can be demonstrated by examining their ability to form membrane channels versus antimicrobial inhibitory effects (Kagan et al., 1990; Wu et al., Biochemistry, 38:7235 (1999a)). In the alpha-helix antimicrobial peptide CEME, the minimum inhibitory concentration (MIC) against bacterial growth is mimicked by its ability to permeabilize phospholipid membranes and electrophysiologic evidence of membrane channel formation (Wu et al., 1999a). In contrast, the MIC of bactenecin is considerably lower than the concentrations required to cause membrane permeabilization and pore formation, an effect which required substantially higher doses of bactenecin than for may other antimicrobial peptides. This is likely due to the fact that bactenecin has a greater affinity for the lipopolysaccharride-laden outer membrane of bacteria and considerably less affinity for eukaryotic cell-type phospholipid layers (Wu et al., J. Biol. Chem., 274:29 (1999b)). This characteristic of cyclic bactenecin may also help to provide a wide therapeutic window and greater safety when used in contact with mammalian cell types than other antimicrobial peptides.

Membrane pore formation may be due to insertion of peptide monomers into membranes and self-assembly of multimeric pores resulting in significant effects on the permeability barrier function of the membrane (Nygaard et al., Am. J. Respir. Cell Mol. Biol., 8:193 (1993)).

Defensins easily recognized based on the presence of several conserved residues in their sequences, including six invariant cysteines arranged to form three disulfide bonds. The cathelicidin peptides show structural variety, however the evolutionary relationship of these peptides can be clearly inferred based on sequences of their intracellular storage forms, which show that these diverse antimicrobial peptides are attached to a highly conserved N-terminal propiece.

Cathelicidin genes are organized into four exons, with the coding sequence for the preproregion contained in exons 1-3, and the region encoding the varied antimicrobial domain in exon 4. Peptides derived from cathelicidins are representative of all the structural groups of the known antimicrobial peptides. They show in general a potent, rapid, and broad spectrum antimicrobial activity, and the ability to bind to and neutralize endotoxin. Their activities and localization in neutrophils and at a mucosal surfaces suggest they could contribute substantially to systemic and local host defense. Peptides that may assume an α-helical conformation are most common among natural antimicrobial peptides, also including the cathelicidin peptides.

A group of cathelicidin peptides comprises linear peptides with one or two predominant amino acids and with repeating motifs. The first peptides with these features to be isolated and sequenced were Pro/Arg-rich Bac5 and Bac7 from bovine neutrophil leukocytes. Subsequently, a member of this group name PR-39 was purified from porcine intestine and neutrophils. A common feature of Pro- and Arg-rich peptides is their high content of praline (from 33 to 49%) and arginine (from 13 to 33%). A 13-residue peptide-amide with a remarkable sequence because of its high content of tryptophan and praline was isolated from the cytoplasmic granules of bovine neutrophils and cloned from myeloid cDNA. This peptide was named indolicidin. The dodecapeptide, also called bactenecin, was isolated from bovine neutrophils and later recognized as a member of the cathelicidin family. The two cysteines were initially suggested to be engaged in an intramolecular disulfide bond. More recent mass spectrometry studies indicated the presence of intermolecular, rather that intramolecular disulfide bridges.

Protegrins are small cationic peptides (16-18 residues) identified in pigs and characterized by two intrachain disulfide bonds and an amidated C-terminus.

Defensins have 28-42 amino acids and including six to eight conserved cysteine residues. Cells of the immune system contain these peptides to assist in killing phagocytized bacteria, for example, in neutrophil granulocytes and almost all epithelial cells. They are highly cationic polypeptides found in lysosomal granules of neutrophil granulocytes. They are thought to be involved in bacterial killing and occur in a third class of granules, the large granules, not found in the neutrophils of most species. Vertebrate defensins have been categorized into α, β and θ defensins. α defensins are produced inside neutrophils and Paneth cells. β defensins are common in epithelial cells, especially airways, skin and the salivary gland. θ defensins have only been found in primate phagocytes. All defensins have been proven to kill at least some kinds of invaders, and they can also attract monocytes and T cells by chemotaxis. Defensins are contained in various secretions throughout the body, including those of the sebaceous gland in the pores of the skin. Those in the skin are referred to as beta-defensins. They are also present in earwax, lungs, and colon.

More than seven hundreds of defense peptides have been isolated. The sequences of defense peptides and related publications are available in the database at http://www.bbcm.u-niv.trieste.it/~tossi/pag1.html. Even though the peptide vary in length, amino acid composition and even primary amino acid sequence, most of them share some common characteristics. As shown in Table 2, they have a high net positive charge at physiological condition and amphiphilic structure and/or hydrophobic character. Defense peptides generally have broad spectrum of activity against Gram-positive and Gram-negative bacteria, fungi, parasites, and even cancer cells. Nevertheless, most of them do not have identical spectrum of antibacterial activity and have considerable selectivity for microorganisms including fungi over eukaryotic cells.

TABLE 2

| Peptide | Sequence |
|---|---|
| Linear | |
| Magainin 2 | GLGKFLHSAKKFGKAFVGEIMNS; SEQ ID NO: 1 |
| Cecropin A | KWKLFKKIEKVGQNIRDGIIKAGPAVAVVGQATQIAK-NH$_2$; SEQ ID NO: 2 |
| Melittin | GIGAVLKVLTTGLPALISWIKRKRQQ-NH$_2$; SEQ ID NO: 3 |
| Pardaxin | GFFALIPKIISSPKFKTLLSAVGSALSSSGEQE; SEQ ID NO: 4 |
| LL-37 | LLGDFFRKSKEKIGKEFKRIVQRIKDFLRNLVPRTES; SEQ ID NO: 5 |
| PR 39 | RRRPRPPYLPRPRPPPFFPPRLPPRIPPGFPPRFPPRFP-NH$_2$; SEQ ID NO: 6 |
| Indolicidin | ILPWKWPWWPWRR-NH$_2$; SEQ ID NO: 7 |
| One-disulfide bridge | |
| Brevinin 1 | FLPLLAGLAANFLPKIFCKITRKC; SEQ ID NO: 8 |
| Bactenecin | RLCRIVVIRVCR; SEQ ID NO: 9 |
| Two-disulfide bridges | |
| Tachyplesin 1 | KWCFRVCYRGICYRRCR-NH$_2$; SEQ ID NO: 10 |
| Protegrin | RGGRLCYCRRRFCVCVGR; SEQ ID NO: 11 |
| Three-disulfide bridges | |
| HNP-1 | ACYCRIPACIAGERRYGTCIYQGRLWAFCC; SEQ ID NO: 12 |
| Insect defensinA | ATCDLLSGTGINHSACAAHCLLRGNRGGYCNGKGVCVCRN; SEQ ID NO: 13 |

The present invention is not limited to any particular defensin. Indeed, media comprising a variety of defensins are contemplated. Representative defensins are provided in Tables 3 and 4 below. In general, defensins are a family of highly cross-linked, structurally homologous antimicrobial peptides found in the azurophil granules of polymorphonuclear leukocytes (PMN's) with homologous peptides being present in macrophages (e.g., Selsted et al., *Infect. Immun.*, 45:150 (1984)). Originally described as "Lysosomal Cationic Peptides" in rabbit and guinea pig PMN (Zeya et al., *Science*, 154:1049 (1966); Zeya et al., *J. Exp. Med.*, 127:927 (1968); Zeya et al., *Lab. Invest.*, 24:229 (1971); Selsted et al., 1984), this mixture was found to account for most of the microbicidal activity of the crude rabbit PMN extract against various microorganisms (Zeya et al., 1966; Lehrer et al., *J. Infect. Dis.*, 136:96 (1977); Lehrer et al., *Infect. Immun.*, 11:1226 (1975)). Six rabbit neutrophil defensins have been individually purified and are designated NP-1, NP-2, NP-3A, NP-3B, NP-4, and NP-5. Their amino acid sequences were determined, and their broad spectra of activity were demonstrated against a number of bacteria (Selsted et al., *Infect. Immun.*, 45:150 (1984)), viruses (Lehrer et al., *J. Virol.*, 54:467 (1985)), and fungi (Selsted et al., *Infect. Immun.*, 49:202 (1985); Segal et al., 151:890 (1985)). Defensins have also been shown to possess mitogenic activity (e.g., Murphy et al., *J. Cell. Physiol.*, 155:408 (1993)).

Four peptides of the defensin family have been isolated from human PMN's and are designated HNP-1, HNP-2, HNP-3, and HNP-4 (Ganz et al., *J. Clin. Invest.*, 76:1427 (1985); Wilde et al., *J. Biol. Chem.*, 264:11200 (1989)). The amino acid sequences of HNP-1, HNP-2, and HNP-3 differ from each other only in their amino terminal residues, while each of the human defensins are identical to the six rabbit peptides in 10 or 11 of their 29 to 30 residues. These are the same 10 or 11 residues that are shared by all six rabbit peptides. Human defensin peptides have been shown to share with the rabbit defensins a broad spectrum of antimicrobial activity against bacteria, fungi, and enveloped viruses (Ganz et al., 1985).

Defensin peptides suitable for use in the compositions and devices of the present invention include natural defensin peptides isolated from known cellular sources, synthetic peptides produced by solid phase or recombinant DNA techniques, and defensin analogs which may be smaller peptides or other molecules having similar binding and biological activity as the natural defensin peptides (e.g., peptide mimetics). Methods for the purification of defensin peptides are described in U.S. Pat. Nos. 4,543,252; 4,659,692; and 4,705,777, the disclosures of which are incorporated herein by reference.

In some embodiments, suitable synthetic peptides include all or part of the amino acid sequence of a known peptide, more preferably incorporating at least some of the conserved regions identified in Table 3. In particularly preferred embodiments, the synthetic peptides incorporate at least one of the conserved regions, more usually incorporating two of the conserved regions, preferably conserving at least three of the conserved regions, and more preferably conserving four or more of the conserved regions. In preferred embodiments, the synthetic peptides comprise fifty amino acids or fewer, although there may be advantages in increasing the size of the peptide above that of the natural peptides in certain instances. In certain embodiments, the peptides have a length in the range from about 10 to 50 amino acids, preferably being in the range from about 10 to 40 amino acids, and most preferably being in the range from about 30 to 35 amino acids which corresponds generally to the length of the natural defensin peptides.

In some cases, it may be desirable to incorporate one or more non-natural amino acids in the synthetic defensin peptides of the present invention. In some embodiments, non-natural amino acids comprise at least an N-terminus and a C-terminus and have side chains that are either identical to or chemically modified or substituted from a natural amino acid counterpart. An example of a non-natural amino acid is an optical isomer of a naturally-occurring L-amino acid, such as a peptide containing all D-amino acids. Examples of the synthesis of peptides containing all D-amino acids include Merrifield et al., *Ciba Found Symp.*, 186:5 (1994); Wade et al., *Proc. Natl. Acad. Sci. USA*, 87:4761 (1990); and U.S. Pat. No. 5,792,831, which is herein incorporated by reference. Examples of chemical modifications or substitutions include hydroxylation or fluorination of C—H bonds within natural amino acids. Such techniques are used in the manufacture of drug analogs of biological compound.

TABLE 3

| Name | Sequence |
| --- | --- |
| lingual antimicrobial peptide precursor (Magainin) | mrlhhlllallflvlsagsgftqgvrnsqscrrnkgicvpircp gsmrqigtclgaqvkccrrk; SEQ ID NO: 14 |
| antimicrobial peptide PGQ | gvlsnvigylkklgtgalnavlkq; SEQ ID NO: 15 |
| Xenopsin | mykgiflcvllavicanslatpssdadedndeveryvrgw askigqtlgkiakvglkeliqpkreamlrsaeaqgkrpwil; SEQ ID NO: 16 |
| magainin precursor | mfkglficsliavicanalpqpeasadedmderevrgigk flhsagkfgkafvgeimkskrdaeaavgpeafadedldere vrgigkflhsakkfgkafvgeimnskrdaeavgpeafade dlderevrgigkflhsakkfgkafvgeimnskrdaeavgp eafadedlderevrgigkflhsakkfgkafvgeimnskrd aeavgpeafadedfderevrgigkflhsakkfgkafvgei mnskrdaeavgpeafadedlderevrgigkflhsakkfgk afvgeimnskrdaeavddrrwve; SEQ ID NO: 17 |
| tachyplesin I | kwcfrvcyrgicyrrcr; SEQ ID NO: 18 |
| tachyplesin II | rwcfrvcyrgicyrkcr; SEQ ID NO: 19 |
| buforin I | msgrgkqggkvrakaktrssraglqfpvgrvhrllrkgny aqrvgagapvylaavleyltaeilelagnaardnkktrii prhlqlavrndeelnkllggvtiaqggvlpniqavllpkt esskpaksk; SEQ ID NO: 20 |
| buforin II | trssraglqfpvgrvhrllrk; SEQ ID NO: 21 |
| cecropin A | mnfvrilsfvfalvlalgavsaapeprwklfkkiekvgrn vrdglikagpaiavigqakslgk; SEQ ID NO: 22 |
| cecropin B | mnfakilsfvfalvlalsmtsaapeprwkifkkiekmgrn irdgivkagpaievlgsakaigk; SEQ ID NO: 23 |
| cecropin C | mnfykifvfvalilaisigqseagwlkklgkrierigqht rdatiqglgiaqqaanvaatarg; SEQ ID NO: 24 |
| cecropin P1 | swlsktakklensakkrisegiaiaiqggpr; SEQ ID NO: 25 |
| indolicidin | ilpwkwpwwpwrr; SEQ ID NO: 26 |
| nisin | itsislctpgcktgalmgcnmktatchcsihvsk; SEQ ID NO: 27 |
| ranalexin | flgglikivpamicavtkkc; SEQ ID NO: 28 |
| lactoferricin B | fkcrrwqwrmkklgapsitcvrraf; SEQ ID NO: 29 |
| protegrin-1 | rggrlcycrrrfcvcvgrx; SEQ ID NO: 30 |
| protegrin-2 | ggrlcycrrrfcicvg; SEQ ID NO: 31 |
| histatin precursor | mkffvfalilalmlsmtgadshakrhhgykrkfhekhhsh rgyrsnylydn; SEQ ID NO: 32 |
| histatin 1 | dsheerhhgrhghhkygrkfhekhhshrgyrsnylydn; SEQ ID NO: 33 |

TABLE 3-continued

| Name | Sequence |
|---|---|
| dermaseptin | alwktmlkklgtmalhagkaalgaaadtisqtq;<br>SEQ ID NO: 34 |
| dermaseptin 2 | alwftmlkklgtmalhagkaalgaaantisqgtq;<br>SEQ ID NO: 35 |
| dermaseptin 3 | alwknmlkgigklagkaalgavkklvgaes;<br>SEQ ID NO: 36 |
| misgurin | rqrveelskfskkgaaarrrk;<br>SEQ ID NO: 37 |
| melittin | gigavlkvlttglpaliswisrkkrqq;<br>SEQ ID NO: 38 |
| pardaxin-1 | gffalipkiissplfktllsavgsalsssgeqe;<br>SEQ ID NO: 39 |
| pardaxin-2 | gffalipkiisspifktllsavgsalsssggqe;<br>SEQ ID NO: 40 |
| bactenecin 5 precursor | metqraslslgrcslwlllllglvlpsaaqalsyreavlr<br>avdqfhersseanlyleldptpnddldpgtrkpvsfrv<br>ketcprtsqqpleqcdfkenglvkqcvgttldpsndqf<br>dincnelqsvrfrppirrpirppfyppfrppirppifpp<br>irpfrppgpfpgrr;<br>SEQ ID NO: 41 |
| bactenecin precursor | metpraslslgrwslwlllllglalpsasaqalsyreavlr<br>avdqlneqssepniyrlleldqppqddedpdskrvsfrv<br>ketvcsrttqqppeqcdfkengllkrcegtvtldqvrgnf<br>ditcnnhqsiritkcipwappqaarlcrivvirvr;<br>SEQ ID NO: 42 |
| ceratotoxin A | sigsalkkalpvakkigkialpiakaalp;<br>SEQ ID NO: 43 |
| ceratotoxin B | sigsafkkalpvakkigkaalpiakaalp;<br>SEQ ID NO: 44 |
| cathelicidin antimicrobial peptide | mktqrnghslgrwslvlllglvmplaiiaqvlsykeavl<br>raidginqrssdanlyrlldldprptmdgdpdtpkpvsft<br>vketvcprttqqspedcdfkkdglvkrcmgtvtlnqargs<br>fdiscdkdnkrfallgdffrkskekigkefkrivqrikdf<br>lrnlvprtes;<br>SEQ ID NO: 45 |
| myeloid cathelicidin 3 | metqrntrclgrwsplllllglvippattqalsykeavlr<br>avdglnqrssdenlyrlleldplpkgdkdsdtpkpvsfmv<br>ketvcprimkqtpeqcdfkenglvkqcvgtvildpvkdyf<br>dascdepqrvkrfhsvgsliqrhqqmirdkseatrhgiri<br>itrpklllas;<br>SEQ ID NO: 46 |
| myeloid antimicrobial peptide BMAP-28 | metqraslslgrwslwlllllglalpsasaqalsyreavlr<br>avdqlneksseanlyrlleldpppkeddenpnpkpvsfr<br>vketvcprtsqqspeqcdfkengllkecvgtvtldqvgsn<br>fditcavpqsvgglrslgrkilrawkkygpiivpiirig;<br>SEQ ID NO: 47 |
| myeloid cathelicidin 1 | Metqrntrclgrwsplllllglvippattqalsykeavl<br>ravdglnqrssdenlyrlleldplpkgdkdsdtppvsfmv<br>ketvcprimkqtpeqcdfkenglvkqcvgtvilgpvkdhf<br>dvscgepqrvkrfgrlaksflrmrillprrkilas;<br>SEQ ID NO: 48 |
| SMAP 29 | metqraslslgrcslwlllllglalpsasaqvlsyreavlr<br>aadqlneksseanlyrlleldpppkqddensnikpvsfr<br>vketvcprtsqqpaeqcdfkengllkecvgtvtldqvrnn<br>fditcaepqsvrglrrlgrkiahgvkkygptvlriiriag;<br>SEQ ID NO: 49 |
| BNP-1 | rlcrivvircr;<br>SEQ ID NO: 50 |
| HNP-1 | acycripaciagerrygtciyqgrlwafcc;<br>SEQ ID NO: 51 |

TABLE 3-continued

| Name | Sequence |
|---|---|
| HNP-2 | cycripaciagerrygtciyqgrlwafcc;<br>SEQ ID NO: 52 |
| HNP-3 | dcycripaciagerrygtciyqgrlwafcc;<br>SEQ ID NO: 53 |
| HNP-4 | vcscrlvfcrrtelrvgncliggvsftycctrv;<br>SEQ ID NO: 54 |
| NP-1 | vvcacrrralclprerragfcrirgrihplccrr;<br>SEQ ID NO: 55 |
| NP-2 | vvcacrrralclplerragfcrirgrihplccrr;<br>SEQ ID NO: 56 |
| NP-3A | gicacrrrfcpnserfsgycrvngaryvrccsrr;<br>SEQ ID NO: 57 |
| NP-3B | grcvcrkqllcsyrerrigdckirgvrfpfccpr;<br>SEQ ID NO: 58 |
| NP-4 | vsctcrrfscgfgerasgsctvnggvrhtlccrr;<br>SEQ ID NO: 59 |
| NP-5 | vfctcrgflcgsgerasgsctingvrhtlccrr;<br>SEQ ID NO: 60 |
| RatNP-1 | vtcycrrtrcgfrerlsgacgyrgriyrlccr;<br>SEQ ID NO: 61 |
| Rat-NP-3 | cscrysscrfgerllsgacrlngriyrlcc;<br>SEQ ID NO: 62 |
| Rat-NP-4 | actcrigacvsgerltgacglngriyrlccr;<br>SEQ ID NO: 63 |
| GPNP | rrcicttrtcrfpyrrlgtcifqnrvytfcc;<br>SEQ ID NO: 64 |
| beta<br>defensin-3 | mrihyllfallflflvpvpghggiintlqkyycrvrggrc<br>avlsclpkeeqigkcstrgrkccrrkk;<br>SEQ ID NO: 65 |
| theta<br>defensin-1 | rcictrgfcrclcrrgvc;<br>SEQ ID NO: 66 |
| defensin<br>CUA1 | mkssmkmfaalllvvmcllanemggplvveartcesqshk<br>fkgtclsdtncanvchserfsggkcrgfrrrcfctthc;<br>SEQ ID NO: 67 |
| defensin<br>SD2 | mkssmkmfaalllvvmcllanemggplvveartcesqshk<br>fkgtclsdtncanvchserfsggkcrgfrrrcfctthc;<br>SEQ ID NO: 68 |
| neutrophil<br>defensin 2 | acycripaclagerrygtcfymgrvwafcc;<br>SEQ ID NO: 69 |
| 4 KDA<br>defensin | gfgcpfhqgachrhcrsirrrggycaglfkqtctctcyr;<br>SEQ ID NO: 70 |
| defensin | gfgcpnnyqchrhcksipgrcggycggxhrlrctcyrc;<br>SEQ ID NO: 71 |
| defensin<br>AMP1 | dgvklcdvpsgtwsghcgssskcsqqckdrehfayggach<br>yqfpsvkcfckrqc;<br>SEQ ID NO: 72 |
| defensin<br>AMP1 | nlcerasltwtgncgntghcdtqcrnwesakhgachkrgn<br>wkcfcyfnc;<br>SEQ ID NO: 73 |
| cysteine-rich<br>cryptdin-1<br>homolog | mkklvllfalvllafqvqadsiqntdeetkteeqpgekdq<br>avsvsfgdpqgsalqdaalgwgrrcpqcpcpscpsc prc<br>prcprckcnpk;<br>SEQ ID NO: 74 |
| beta-<br>defensin-9 | qgvrnfvtcrinrgfcvpircpghrrqigtclgpqikccr;<br>SEQ ID NO: 75 |

TABLE 3-continued

| Name | Sequence |
|---|---|
| beta-defensin-7 | qgvrnfvtcrinrgfcvpircpghrrqigtclgprikccr; SEQ ID NO: 76 |
| beta-defensin-6 | qgvrnhvtcriyggfcvpircpgrtrqigtcfgrpvkccrrw; SEQ ID NO: 77 |
| beta-defensin-5 | qvvrnpqscrwnmgvcipiscpgnmrqigtcfgprvpcc; SEQ ID NO: 78 |
| beta-defensin-4 | Qrvrnpqscrwnmgvcipflcrvgmrqigtcfgprvpccr; SEQ ID NO: 79 |
| beta-defensin-3 | Qgvrnhvtcrinrgfcvpircpgrtrqigtcfgprikccrsw; SEQ ID NO: 80 |
| beta-defensin-10 | Qgvrsylscwgnrgicllnrcpgrmrqigtclaprvkccr; SEQ ID NO: 81 |
| beta-defensin-13 | Sgisgplscgrnggvcipircpvpmrqigtcfgrpvkccrs; SEQ ID NO: 82 |
| beta-defensin-1 | Dfaschtnggiclpnrcpghmiqigicfrprvkccrsw; SEQ ID NO: 83 |
| coleoptericin | slqggapnfpqpsqqnggwqvspdlgrddkgntrgqieiq nkgkdhdfnagwgkvirgpnkakpthvggtyrr; SEQ ID NO: 84 |
| beta defensin-3 | mrihyllfallflflvpvpghggiintlqkyycrvrggrc avlsclpkeeqigkcstrgrkccrrkk; SEQ ID NO: 85 |
| defensin C | Atcdllsgfgvgdsacaahciargnrggycnskkvcvcrn; SEQ ID NO: 86 |
| defensin B | Gfgcpndypchrhcksipgryggycggxhrlrctc; SEQ ID NO: 87 |
| sapecin C | Atcdllsgigvqhsacalhcvfrgnrggyctgkgicvcrn; SEQ ID NO: 88 |
| macrophage antibiotic peptide MCP-1 | mrtlallaaillvalqaqaehvsvsidevvdqqppqaedq dvaiyvkehessalealgvkagvvcacrraclprerrag fcrirgrihplccrr; SEQ ID NO: 89 |
| cryptdin-2 | mkplvllsalvllsfqvqadpiqntdeetkteeqsgeedq avsvsfgdregaslqeeslrdlvcycrtrgckrrermngt crkghlmytlcc; SEQ ID NO: 90 |
| cryptdin-5 | mktfvllsalvllafqvqadpihktdeetnteeqpgeedq avsisfggqegsalheelskklicycrirgckrrervfgt crnifitfyfccs; SEQ ID NO: 91 |
| cryptdin 12 | Lrdlvcycrargckgrermngtcrkghllymlccr; SEQ ID NO: 92 |
| defensin | Atcdilsfqsqwvtpnhagcalhcvikgykggqckitvchc rr; SEQ ID NO: 93 |
| defensin R-5 | Vtcycrstrcgfrerlsgacgyrgriyrlccr; SEQ ID NO: 94 |
| defensin R-2 | Vtcscrtsscrfgerlsgacrlngriyrlcc; SEQ ID NO: 95 |
| defensin NP-6 | Gicacrrrfclnfeqfsgycrvngaryvrccsrr; SEQ ID NO: 96 |
| beta-defensin-2 | mrvlyllfsflfiflmplpgvfggisdpvtclksgaichp vfcprrykqigtcglpgtkccckkp; SEQ ID NO: 97 |
| beta- | mrvlyllfsflfiflmplpgvfggigdpvtclksgaichp |

TABLE 3-continued

| Name | Sequence |
|---|---|
| defensin-2 | vfcprrykqigtcglpgtkcckkp;<br>SEQ ID NO: 98 |
| beta-defensin-1 | mrtsylllftlclllsemasggnfltglghrsdhyncvss<br>ggqclysacpiftkiqgtcyrgkakcck;<br>SEQ ID NO: 99 |
| beta-defensin-1 | mrlhhlllvlfflvlsagsgftqgirsrrschrnkgvcal<br>trcprnmrgigtcfgppvkccrkk;<br>SEQ ID NO: 100 |
| beta defensin-2 | mrlhhlllalfflvlsagsgftqgiinhrscyrnkgvcap<br>arcprnmrqigtchgppvkccrkk;<br>SEQ ID NO: 101 |
| defensin-3 | mrtlvilaaillvalqaqaeplqartdeataaqeqiptdn<br>pevvvslawdeslapkdsvpglrknmacycipaclager<br>rygtcfyrrrvwafcc;<br>SEQ ID NO: 102 |
| defensin-1 | mrtlvilaaillvalqaqaeplqartdeataaqeqiptdn<br>pevvvslawdeslapkdsvpglrknmacycripaclager<br>rygtcfylgrvwafcc;<br>SEQ ID NO: 103 |
| neutrophil defensin 1 | vtcfcrrrgcasrerhigycrfgntiyrlccrr;<br>SEQ ID NO: 104 |
| neutrophil defensin 1 | cfckrpvcdsgetqigycrlgntfyrlccrq;<br>SEQ ID NO: 105 |
| Gallinacin 1-alpha | grksdcfrkngfcaflkcpyltlisgkcsrfhlcckriw;<br>SEQ ID NO: 106 |
| defensin | vtcdllsfeakgfaanhslcaahclaigrrggscergvcicrr;<br>SEQ ID NO: 107 |
| neutrophil cationic peptide 1 | rrcicttrtcrfpyrrlgtcifqnrvytfcc;<br>SEQ ID NO: 108 |

TABLE 4

| Name | Sequence |
|---|---|
| HNP-1 | ACYCRIPACIAGERRYGTCIYQGRLWAFCC;<br>SEQ ID NO: 109 |
| HNP-2 | CYCRIPACIAGERRYGTCIYQGRLWAFCC;<br>SEQ ID NO: 110 |
| HNP-3 | DCYCRIPACIAGERRYGTCIYQGRLWAFCC;<br>SEQ ID NO: 111 |
| HNP-4 | VCSCRLVFCRRTELRVGNCLIGGVSFTYCCTRV;<br>SEQ ID NO: 112 |
| NP-1 | VVCACRRALCLPRERRAGFCRIRGRIHPLCCRR;<br>SEQ ID NO: 113 |
| NP-2 | VVCACRRALCLPLERRAGFCRIRGRIHPLCCRR;<br>SEQ ID NO: 114 |
| NP-3A | GICACRRRFCPNSERFSGYCRVNGARYVRCCSRR;<br>SEQ ID NO: 115 |
| NP-3B | GRCVCRKQLLCSYRERRIGDCKIRGVRFPFCCPR;<br>SEQ ID NO: 116 |
| NP-4 | VSCTCRRFSCGFGERASGSCTVNGVRHTLCCRR;<br>SEQ ID NO: 117 |
| NP-5 | VFCTCRGFLCGSGERASGSCTINGVRHTLCCRR;<br>SEQ ID NO: 118 |
| RatNP-1 | VTCYCRRTRCGFRERLSGACGYRGRIYRLCCR;<br>SEQ ID NO: 119 |
| Rat-NP-3 | CSCRYSSCRFGERLLSGACRLNGRIYRLCC;<br>SEQ ID NO: 120 |
| Rat-NP-4 | ACTCRIGACVSGERLTGACGLNGRIYRLCCR;<br>SEQ ID NO: 121 |
| GPNP | RRCICTTRTCRFPYRRLGTCIFQNRVYTFCC;<br>SEQ ID NO: 122 |

Neuropeptides

Neuropeptides useful in the compositions and devices of the invention include mammalian tachykinins including but are not limited to Substance P (SP), neurotensin, neurokinins (NK), e.g., neurokinin A and neurokinin B, and hemokinin/endokinin (EK) (Table 5). A number of structure/activity studies of vertebrate TKs revealed the amino acid residues typical for SP, NKA, and NKB; SP-type peptides contain an aromatic amino acid (Phe or Tyr) at position 4 from the C-terminus, whereas a branched aliphaticresideu (Ile or Val) is located at the corresponding position of NKA and NKB. Likewise, a neutral or basic amino acid occupies position 7 from the C-terminus of SP and its submammalian counterparts, and an acidic residue is found at this position NKA and NKB. These amino acids play a crucial role in their binding selectivity to TK receptors.

The above TKs are encoded by the preprotachykinin A (PPTA or TAC1) or PPTB (or TAC3) genes.

TABLE 5

| Species | Peptide | Sequence |
|---|---|---|
| Mammals | Substance P | RPKPQQFFGLM-NH$_2$; SEQ ID NO: 123 |
| | Neurokinin A | HKTDSFVGLM-NH$_2$; SEQ ID NO: 124 |
| | Neurokinin B | DMHDFVGLM-NH$_2$; SEQ ID NO: 125 |
| | Neuropeptide-γ | AGHQISHKRHKTDSFVGLM-NH$_2$; SEQ ID NO: 126 |
| | Neuropeptide K | DADSSIEKQQVALLKALYGHGQISHKRHKTDSFVGLM-NH$_2$; SEQ ID NO: 127 |
| Human | Endokinin A/B* | GKASQFFGLM-NH$_2$; SEQ ID NO: 128 |
| | Endokinin C* | KKAYQLEHTFQGLL-NH$_2$; SEQ ID NO: 129 |
| | Endokinin D* | VGAYQLEHTFQGLL-NH$_2$; SEQ ID NO: 130 |

Substance P is a short-chain polypeptide that functions as a neurotransmitter and as a neuromodulator. Substance P is an 11-amino acid polypeptide with the sequence: Arg Pro Lys Pro Gln Gln Phe Phe Gly Leu Met NH$_2$. In the central nervous system, substance P has been associated in the regulation of mood disorders, anxiety, stress, reinforcement, neurogenesis, respiratory rhythm, neurotoxicity, nausea/emesis and pain, and has effects as a potent vasodilator. This is caused by the release of nitric oxide from the endothelium. Its release can cause hypotension. The endogenous receptor for Substance P is neurokinin 1 receptor (NK1-receptor, NK1R). Substance P is involved in the transmission of pain impulses from peripheral receptors to the central nervous system.

Neurotrophins

The neurotrophins (NTs) include structurally and functionally related molecules, such as nerve growth factor (NGF), which influences the proliferation, differentiation, survival and death of neuronal cells. Nerve growth factor (NGF), brain-derived neurotrophic factor (BDNF), neurotrophin-3 (NT-3), neurotrophin-4/5 (NT-4/5), glia cell derived growth factor (GCDGF), and leukemia inhibitory factor (LIF) are members of the neurotrophin (NT) gene family, which may include neurotrophin-like factors, e.g., EGF. NGF maintains the survival of cholinergic neurons of the basal forebrain system, nociceptive dorsal root ganglion neurons and some third-order sympathetic neurons, while BDNF supports cholinergic, dopaminergic neurons as well as those containing 5-hydroxytryptamine and neuropeptides. NT-3 was shown to prevent the death of adult central noradrenergic neurons in vivo.

BDNF can promote survival, but not differentiation, of neurons arising from the forebrain subependymal zone. Conversely, BDNF has been reported to enhance both survival and differentiation of neurons derived from EGF-responsive postnatal hippocampal stem cells. NGF, in conjunction with bFGF, stimulates proliferation of striatal precursor cells.

BDNF and NGF show no effects on cell proliferation (if NSCs are cultured with EGF and BDNF or NGF) when compared to EGF controls and removal of EGF is permissive for the differentiating effects of BDNF and NGF. The actions of BDNF and NGF on EGF-responsive clonal neurosphere differentiation are most probably due to induced differentiation, and not cell survival or proliferation.

Neurotrophins are synthesized as precursors of 30-35 kDa, then proteolytically processed, either intracellularly by furin or prohormone convertases extracellularly by plasmin or metalloproteases at the level of a highly conserved dibasic amino acid motif.

Neurotrophins recognize a complex receptor system consisting of tyrosine kinase receptors of the tropomyosine-related kinase (Trk) family, and the structurally unrelated p75$^{NTR}$, a member of the tumor necrosis factor receptor superfamily. Each neurotrophin binds with a high affinity (about 10$^{-11}$ M) to a specific Trk receptor; TrkA is the receptor for NGF, TrkB for BDNF and NT4/5, and TrkC for NT3 (NT3 can also bind to TrkA and TrkB under specific cellular contexts). By contrast, all neurotrophins bind to the receptor p75$^{NTR}$, with a dissociation constant in the nanomolar range.

It has been proposed p75$^{NTR}$ receptor could function as a quality control receptor increasing the likelihood of apoptosis when neurotrophins are withdrawn, or their proteolytic processing is incomplete, or when a cell is exposed to a neurotrophin other than the one appropriate for the Trk expressed. Binding of mature neurotrophins to their specific Trk receptors causes receptor dimerization, activation of the intrinsic tyrosine kinase domain by transphosphorylation, and the initiation of several downstream signaling cascades.

Neurotrophins useful in the compositions and devices of the invention include functional mimetics thereof such as those disclosed in Peleshok et al. (*Biochem. Soc. Trans.*, 34:612 (2006)), the disclosure of which is incorporated by reference herein.

Other Media Components

In certain embodiments, a number of other components are utilized in the media of the present invention to provide the proper balance of electrolytes, a physiological pH, proper oncotic pressure, etc. Therefore, it is contemplated that the media comprises one or more components selected from one or more of the following general groups: 1) electrolytes; 2) oncotic agents; 3) buffers; 4) energy sources; 5) impermeant anions; 6) free radical scavengers; and/or 7) ATP.

In some embodiments of the present invention, the media comprises electrolytes (e.g., sodium, potassium, calcium, magnesium, chloride, sulfate, bicarbonate, and phosphate) in concentrations approximating those found in blood plasma. For example, in some embodiments, potassium is provided as KH$_2$PO$_4$ in range from about 10 to 50 mM, preferably about 25 mM; magnesium is provided as magnesium gluconate in a range of from about 1 to 10 mM, preferably about 5 mM; sodium is provided as sodium gluconate in a range of from about 50 mM to about 150 mM, preferably about 105 mM; and calcium and chloride are provided as CaCl$_2$ in a range of from about 0.1 to 5.0 mM, preferably about 0.5 mM.

In other embodiments, the concentration of individual electrolytes may be varied from physiological concentrations. For example, it is known that membrane pumps of cells are turned off during hypothermia. As a result, potassium and sodium exchange passively across the cell membrane. The media can be adjusted to compensate for the influx of sodium and efflux of potassium by providing potassium in a range of from about 35 to 45 mM and sodium in a range of from about 80 to 120 mM. In further embodiments of the present invention, divalent cations can be included in an amount sufficient to displace or block the effect of calcium ions at the cellular membrane. Accordingly, in some embodiments, Ca$^{++}$ is provided in a range of from about 0.01 mM to 0.1 mM, preferably from about 0.01 to 0.07 mM, and $Mg^{++}$ is provided in a range of from about 1 mM to 10 mM, preferably about 2.5 mM to 7.5 mM.

The oncotic agent is included in an amount sufficient to maintain oncotic pressure equivalent to that of blood plasma. Examples of oncotic agents include, but are not limited to, hydroxyethyl starch, cyclodextrins, and dextran (e.g., Dextran 30, 40, or 50).

In some embodiments of the present invention, the media comprises at least one buffer. In preferred embodiments, the concentration of buffer(s) is sufficient to maintain the pH of the media at a range of from about 7.0 to 8.0 at 10° C., preferably from about 7.4 to 7.8. The present invention is not limited to the use of any particular buffer. Indeed, the use of a variety of synthetic and other buffers is contemplated. Examples of suitable buffers include, but are not limited to, N-2-hydroxyethylpiperazine-N'-2-hydroxypropanesulfonic acid (HEPES), 3-(N-morpholino)propanesulfonic acid (MOPS), N-tris(hydroxymethyl)methyl-2-aminoethanesulfonic acid; 2-((2-hydroxy-1,1-bis(hydroxymethyl)ethyl) amino)ethanesulfonic acid (TES), 3-(N-tris(hydroxy-methyl)methylamino)-2-hydro-xypropanesulfonic acid (TAPSO), 4-(2-hydroxyethyl)-1-piperazinepropanesulfonic acid (EPPS), pH range 7.3-8.7, and tris(hydroxymethyl)aminomethane (THAM), $HCO_3$, and $H_2PO_4$.

In some embodiments of the present invention, the media further comprises one or more energy or nutrition sources. Examples of energy sources include, but are not limited to, sucrose, fructose, glucose, and dextran. Preferably, the concentration of the energy source is from about 1 mM to 20 mM, most preferably about 10 mM.

Indeed, a variety of impermeant anions are contemplated, including, but not limited to, gluconate and lactobionate. Preferably, the concentration of the impermeant anion is from about 50 to 150 mM, most preferably about 100 mM.

A variety of free radical scavengers are contemplated including, but not limited to, mannitol and glutathione. Preferably, the concentration of the free radical scavenger is from about 1 mM to 10 mM, most preferably about 3 mM.

Indeed, a variety of ATP substrates are contemplated, including, but not limited to, adenosine, fructose, adenine, and ribose. Preferably, the concentration of the ATP substrate is from about 1 mM to 10 mM, most preferably about 5 mM.

Examples of osmotic agents include, but are not limited to, trehalose (α-α-trehalose dihydrate), raffinose, sucrose and mannitol. In preferred embodiments, the osmotic agent is provided at a concentration of about 1 mM to 100 mM, most preferably about 30 mM.

Coatings for Receptacles and Devices

Receptacles and devices may be coated with the trophic factors by dipping the receptacle or device, e.g., bead, in a solution or by spraying the device, or other methods of applying a coating having the trophic factors, to a device. For instance, non-thrombogenic and anti-thrombogenic coatings for devices have been developed, e.g., devices coated with polymers having pendant zwitterionic groups, specifically phosphorylcholine (PC) groups, generally described in WO 93/01221, or those described in WO 98/30615. The polymers coated onto the device have pendant crosslinkable groups which are subsequently crosslinked by exposure to suitable conditions, generally heat and/or moisture. Specifically a trialkoxysilylalkyl group reacts with pendant groups of the same type and/or with hydroxyalkyl groups to generate intermolecular crosslinks, which may lead to reduced thrombogenicity. Other coatings are described in Topol and Serruys in *Circulation*, 98:1802, (1998) and McNair et al., *Proceedings of the International Symposium on Controlled Release Bioactive Materials*, pp. 338-339 (1995) (hydrogel polymers having pendant phosphorylcholine groups). The hydrophilic/hydrophobic ratio of the (hydrophilic) phosphorylcholine monomer 2-methacryloyloxyethyl phosphorylcholine (HEMA-PC) and a hydrophobic comonomer may be modified. Crosslinking may be achieved by incorporating a reactive monomer 3-chloro-2-hydroxypropylmethacrylate. Release rates of trophic factors are influenced by the molecular size, solute partitioning and degree of swelling of the polymer.

Other coatings include polyurethanes. The polyurethanes may be modified to control compatibility with the trophic factors. A polyurethane coated device may be contacted with trophic factors in a solvent which swells the polyurethane, whereby the factors are absorbed into the polyurethane. Selection of a suitable solvent takes into account the swellability of the polyurethane and the solubility of the trophic factors in the solvent.

Coatings may include an undercoat having trophic factors and polymer matrix, and an overlying topcoat which partially covers the undercoat. The top coat may be discontinuous in situ, in order to allow for release of the trophic factors from the undercoat. The polymer of the undercoat is, for example, hydrophobic biostable elastomeric material such as silicones, polyurethanes, ethylene vinyl acetate copolymers, polyolefin elastomers, polyamide elastomers and EPDM rubbers. The top layer may be formed of non-porous polymer such as is as fluorosilicones, polyethylene glycols, polysaccharides and phospholipids.

Curing of a crosslinkable polymer may involve exposure to irradiation, chemical curing agents, catalysts or, more usually raised temperature and/or reduced pressure to acceptable condensation based cross-linking reactions. Drying a liquid composition usually involves raised temperature and/or reduced pressure for a time sufficient to reduce the amount of solvent remaining on the device to undetectable levels or levels at which it will not interfere with subsequent processing steps, or with release of the trophic factors in use, or be toxic to a patient in whom the device is implanted.

In one embodiment, the coating includes an inner layer of an amphiphilic polymer and adhered to the inner layer, crystalline trophic factors. Provision of the crystalline trophic factors may also confer useful release characteristics. The crystalline material may be controlled for a particle size, for instance, to confer desired release characteristics which complement the release of absorbed trophic factors from a polymer coating.

In one embodiment, the coating on at least the outer wall has an inner layer where the polymer is amphiphilic and the topcoat has a non-biodegradable, biocompatible semipermeable polymer. The semipermeable polymer is selected so as to allow permeation of the trophic factors through the top layer when the device is in an aqueous environment. In such an environment, the semipermeable polymer may, for instance, be swollen, and it is in this form that it should allow permeation of the trophic factors. A topcoat may confer desirable controlled release characteristics. Its use is of particular value where coating comprises crystalline trophic factors adhered to an inner layer of amphiphilic polymer. The topcoat in such an embodiment has several functions. It provides a smooth outer profile, minimizes loss of the trophic factors during delivery, provides a biocompatible interface with the blood vessel after implantation and controls release of trophic factors from the device into the surrounding tissue in use. A topcoat is preferably substantially free of the trophic factors prior to implantation of the device. A topcoat may be formed of a second cross-linked amphiphilic polymer. The second amphiphilic polymer may be the same as the first amphiphilic polymer.

A composition to be applied to a receptacle, bead or stent is prepared by conventional methods wherein all composition components are combined and blended. For example, a predetermined amount of a polymer is added to a predetermined amount of a solvent. The term polymer is intended to include a product of a polymerization reaction inclusive of homopolymers, copolymers, terpolymers, etc., whether natural or synthetic, including random, alternating, block, graft, crosslinked, hydrogels, blends, compositions of blends and variations thereof. The solvent can be any single solvent or a combination of solvents capable of dissolving the polymer. The particular solvent or combination of solvents selected is dependent on factors such as the material from which receptacle, bead or device is made and the particular polymer selected. Representative examples of suitable solvents include, but are not limited to, aliphatic hydrocarbons, aromatic hydrocarbons, alcohols, ketones, dimethyl sulfoxide (DMSO), tetrahydrofuran (THF), dihydrofuran (DHF), dimethylacetamide (DMAC), acetates and combinations thereof.

Sufficient amounts of trophic factors are then dispersed in the blended composition of the polymer and the solvent. The trophic factors may be in true solution or saturated in the composition. If the trophic factors is not completely soluble in the composition, operations such as gentle heating, mixing, stirring, and/or agitation can be employed to effect homogeneity of the residues. However, care should be taken to ensure that the use of heat to effect dissolution does not also cause denaturation of a heat-sensitive substance.

The trophic factors may be encapsulated in a sustained delivery vehicle such as, but not limited to, a liposome or a polymeric particle (bead). The preparation and use of such sustained delivery vehicles are well known to those of ordinary skill in the art. Inclusion of the trophic factors in the vehicle should not adversely alter the composition or characteristic of the trophic factors.

Details of methods of coating or impregnating metallic and/or polymeric components are described in the following patents: U.S. Pat. Nos. 6,287,628, 6,506,437, 6,544,582, 6,555,157, 6,585,765, and 6,616,765.

FIG. 1 is an illustration of an embodiment of a portion of an implantable device 100. Implantable device 100 includes a device body 102 having a surface portion 104 on which a coating 106 including the trophic factors is formed. In one embodiment, implantable device 100 is an intravascular device. Examples of the intravascular device include a stent (such as a coronary stent), a transvenous lead (such as a cardiac pacing or defibrillation lead. The stent is further discussed in detail below. In another embodiment, implantable device 100 includes a vascular patch, myocardial patch or a cardiac valve.

Figure 2:
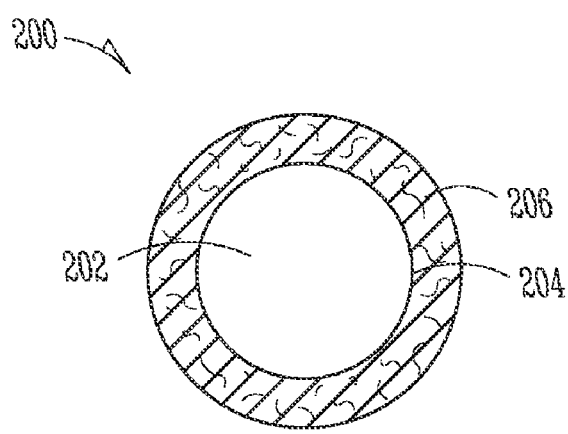
FIG. 2 is an illustration of an embodiment of an article including a bead coated with trophic factors.

FIG. 2 is an illustration of an embodiment of an article 200 including a bead 202 such as a microsphere or nanosphere. Bead 202 includes a surface portion 204 on which a coating 206 including the trophic factors is formed. Bead 202 is made of biocompatible and optionally biodegradable material such as alginate or those disclosed in U.S. Pat. No. 6,120,805, the disclosure of which is incorporated by reference herein in its entirety. In one embodiment, article 200 (the coated biodegradable bead) has a size suitable for administration into the body using an injection device configured for localized agent delivery, such as a percutaneous transluminal catheter or a hollow needle. In one embodiment, article 200 has an approximately spherical shape with a diameter in a range of approximately 10 nanometers to approximately 10 micrometers. In a specific embodiment, the diameter is between about 200 and about 2000 nanometers. The bead is further discussed in detail below.

Stents

In one embodiment, the device is a stent made of a non-biodegradable, biocompatible material such as shape memory metal, or may be elastically self-expanding, for instance, be a braided stent or a balloon expandable stent. In one embodiment of the invention, in which a topcoat is provided, the topcoat may be part of a coherent coating formed over both a stent and a stent delivery device, for instance, a balloon of a balloon catheter from which a balloon expandable stent is delivered. In this case, the balloon may additionally be provided with a coating having the trophic factors, for instance, adsorbed onto parts of its exterior surface between stent struts. Such a device may be produced by loading the stent with the trophic factors after the stent has been mounted onto the delivery catheter.

In one embodiment, contact of the polymer coated stent with a liquid trophic factors containing composition may be by dipping the stent into a body of the stent, and/or by flowing, spraying or dripping a liquid composition onto the stent with immediate evaporation of solvent from the wet stent. Such steps allow good control of trophic factor loading onto the stent, and are particularly useful for forming the crystals of trophic factor at the surface of polymer.

While the stent may be provided with trophic factor coating prior to being mounted onto its delivery device, the stent to be premounted onto its delivery device prior to coating the stent. In this embodiment, it is primarily the outer wall of the stent (as opposed to the inner wall of the stent) which becomes coated with the trophic factors. This method generally results in the trophic factors being coated onto the stent delivery section of the delivery catheter. The outer surface of the delivery catheter with a coating of a trophic factors, is a source to deliver the inhibitor adjacent tissue upon placement of the stent. Generally the delivery catheter is in contact with such tissue for a short period, whereby contact is not maintained for a prolonged period, and limited level of transfer of drug from the balloon takes place.

With reference to FIGS. 3, 4 and 5, in another embodiment of the invention, the implantable device is stent 360 positioned within the vascular system. As shown in FIG. 3, a stent 360 is mounted on a catheter assembly 362 which is used to deliver the stent to implant it in a body lumen, such as a coronary artery, peripheral artery, or other vessel or lumen within the body. The catheter assembly 362 includes a catheter shaft 364 which has a proximal end 366 and a distal end 368. The catheter assembly 362 is configured to advance through the patient's vascular system by advancing over a guide wire 372.

The catheter assembly 362 as illustrated in FIG. 3 is of a rapid exchange type which includes an RX port 370 where the guide wire 372 will exit the catheter. The distal end of the guide wire 372 exits the catheter distal end 368 so that the catheter advances along the guide wire on a section of the catheter between the RX port 370 and the catheter distal end 368. As is known in the art, the guide wire lumen which receives the guide wire 372 is sized for receiving various diameter guide wires to suit a particular application. The stent 360 is mounted on the expandable member 374 and is crimped tightly thereon so that the stent 360 and expandable member 374 present a low profile diameter for delivery through the arteries.

In FIG. 3, a partial cross-section of an artery 376 is shown with a small amount of plaque that has been previously treated by an angioplasty or other repair procedure. Stent 360 is used to repair a diseased or damaged arterial wall which may include plaque 378 as shown in FIG. 3, or a dissection, or a flap which are sometimes found in the coronary arteries, peripheral arteries and other vessels.

In an exemplary procedure to implant the stent 360, the guide wire 372 is advanced through the patient's vascular system by well known methods so that the distal end of the guide wire is advanced past the plaque or diseased area 378. Prior to implanting the stent, the cardiologist may wish to perform an angioplasty procedure or other procedure, i.e., atherectomy, in order to open the vessel and remodel the diseased area. Thereafter, the stent delivery catheter assembly 362 is advanced over the guide wire 372 so that the stent 360 is positioned in the target area. The expandable member or balloon 374 is inflated so that it expands radially outwardly and in turn expands the stent 360 radially outwardly until the stent 360 is apposed to the vessel wall. The expandable member 374 is then deflated and the catheter withdrawn from the patient's vascular system. The guide wire 372 is left in the lumen for post-dilatation procedures, if any, and subsequently is withdrawn from the patient's vascular system. As illustrated in FIG. 4, the balloon 374 is fully inflated with the stent 360 expanded and pressed against the vessel wall, and in FIG. 5, the implanted stent 360 remains in the vessel after the balloon has been deflated and the catheter assembly 362 (FIG. 4) and guide wire 372 have been withdrawn from the patient.

The stent 360 serves to hold open the artery after the catheter is withdrawn, as illustrated by FIG. 5. Due to the formation of the stent from an elongated tubular member, the undulating components of the stent are relatively flat in transverse cross-section. When the stent is expanded, it is pressed into the wall of the artery and accordingly does not interfere with the blood flow through the artery. The stent is pressed into the wall of the artery and will eventually be covered with endothelial cell growth which further minimizes blood flow interference.

In one embodiment, the entire surface of the stent 360 is coated to carry and deliver the trophic factors. In another embodiment, portions of the surfaces of the stent 360, e.g., the tissue contacting portions, are coated to carry the trophic factors. The stent 360 may be formed of either a metal or a polymer material and thus the methods available for medicating the stent 360 are the same as those described above with respect to the metallic and polymeric components of the lead configuration.

Figure 6:
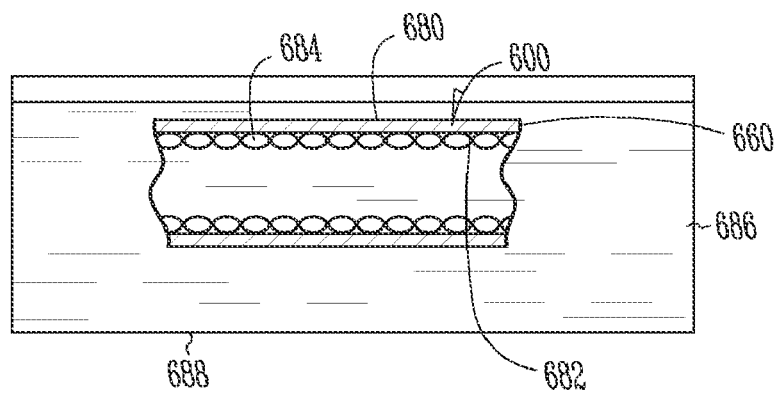
FIG. 6 is an illustration of an embodiment of a stent coated with therapeutic cells in a receptacle having trophic factors.

FIG. 6 is an illustration of an embodiment of a stent 600 in a receptacle 688. Stent 660 includes a stent body 660 having an outer surface 680 and a luminal surface 682. Therapeutic cells 684 are attached onto luminal surface 682. In one embodiment, therapeutic cells 684 are coated onto luminal surface 682. In another embodiment, therapeutic cells 684 are cultured on luminal surface 682. In one embodiment, luminal surface 682 are structured to facilitate the attachment of therapeutic cells 684 onto luminal surface 682. Receptacle 688 is filled with a solution 686 including trophic factors and is configured to allow the entire stent 600 to be within the solution. Examples of receptacle 688 include any device suitable for containing cells, such as syringes, bags, tubes, dishes, boxes, and bottles. In various embodiments, receptacle 688 is used to store cells and/or cell-carrying devices such as stent 600 or any implantable device including a portion onto which stem cells are attached or otherwise incorporated.

Figure 7:
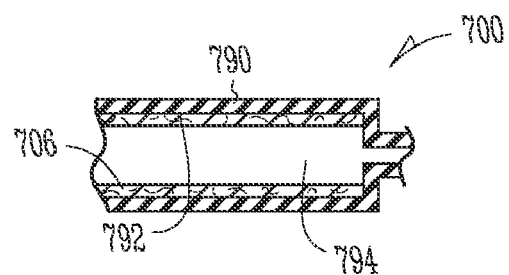
FIG. 7 is an illustration of an embodiment of a therapeutic cell collection device having trophic factors.

FIG. 7 is an illustration of an embodiment of a cell collection device 700 having trophic factors. In the illustrated embodiment, device 700 includes a cell collection syringe including a wall 790 having an interval surface 792. Internal surface 792 forms a chamber 794 to contain the collected stem cells. A layer of traphic factors 706 is coated onto a portion 792 if internal surface 792.

Figure 8:
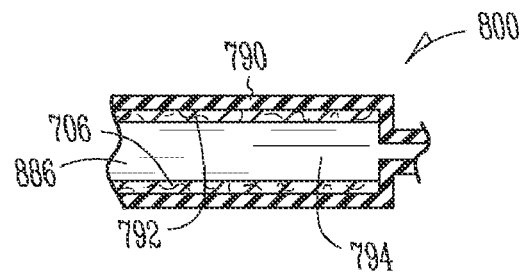
FIG. 8 is an illustration of another embodiment of a therapeutic cell collection device having trophic factors.

FIG. 8 is an illustration of an embodiment of a cell collection device 800 having trophic factors. In the illustrated embodiment, device 800 includes the cell collection syringe illustrated in FIG. 7, with chamber 794 at least partially filled with a solution 886 including trophic factors.

Biocompatible Beads

In one embodiment of the invention, delivery of the trophic factors is achieved using a micro- or nano-carrier, polymeric matrix delivery system such as a micro- or nano-particle, polymeric matrix delivery system. Polymeric materials exhibit several desirable properties including biocompatibility, biodegradability, surface modification, and ease of functionalization of polymers. Polymeric systems allow for a greater control of pharmacokinetic behavior of the loaded active agent.

Microparticles can be microspheres, where the trophic factor is dispersed within a solid polymeric matrix, or microcapsules, where the core is of a different material than the polymeric shell, and the trophic factor is dispersed or suspended in the core, which may be liquid or solid in nature. Nanoparticles are sub-nanosized colloidal structures composed of synthetic or semi-synthetic polymers that vary in size from 10-1000 nm. Depending upon the method of preparation, nanospheres, or nanocapsules can be obtained in which the active agent either is dissolved, entrapped, encapsulated or attached to the nanoparticle matrix. Both non-biodegradable and biodegradable matrices can be used for delivery of the trophic factors. These may be natural or synthetic polymers. The polymer is selected based on the period over which trophic factor release is desired.

Techniques to prepare micro- and nanoparticles from natural and synthetic polymers include electro- and co-electrospinning and specific template methods, so as to allow the incorporation of molecules such as proteins directly during the preparation process. One particular advantage is that proteins can be immobilized in a fluid environment in such a way that they keep their native conformation and corresponding functions. Polymer systems may also be chosen in such a way that the interactions between the trophic factors and the synthetic environment are not detrimental for biological functions and that the access to and the release from the system can be controlled tightly via the nature of the polymer and its internal morphology.

Bioerodible microspheres can be prepared using any of the methods developed for making microspheres for drug delivery, for example, as described by Mathiowitz and Langer, *J. Controlled Release*, 5:13 (1987); Mathiowitz et al., *Reactive Polymers*, 6:275 (1987); and Mathiowitz et al., *J. Appl. Polymer Sci.*, 35:755 (1988), the teachings of which are hereby incorporated by reference. The selection of the method depends on the polymer selection, the size, external morphology, and crystallinity that is desired, as described, for example, by Mathiowitz et al., *Scanning Microscopy*, 4:329 (1990); Mathiowitz et al., *J. Appl. Polymer Sci.*, 45:125 (1992); and Benita et al., *J. Pharm. Sci.*, 73:1721 (1984), the teachings of which are incorporated herein.

In one embodiment, microparticles may be formed of materials including but not limited to alginate, chitosan or poly(DL-lactide-co-caprolactone), poly(DL-lactide-co-glycolide), type I collagen or composites thereof, poly(DL-lactide)(+GF), hollow fiber membranes, polyacrylonitrile-polyvinyl-chloride, and polyacrylonitrile and polysulfone, liposomes, and gelatin nanoparticles (see Guena et al., *Cancer*, 107:459 (2006)). Typical properties of poly(DL-lactide) (PLA)-based materials, such as long degradation time may substantially altered electrospinning of PLA blends with miscible poly(lactide-co-glycolide) (PLGA) random copolymers, poly(lactide-b-ethylene glycol-b-lactide) (PLA-b-PEG-b-PLA) triblock copolymers, and a lactide (used as a hydrolytic catalyst). See also, LaIuppa et al., *J. Biomed. Mater. Res.*, 36:347 (1997)).

Nanoparticles, e.g., composed of lipids or synthetic polymers, protect agents against destruction and control the delivery with well-defined release kinetics, or by a release mechanism which can be triggered by external or internal stimuli. Exemplary nanoparticles include but are not limited to silica nanoparticles (NPs), liposomes, cationic solid-lipid nanoparticle (SLN), polymeric NPs such as PLGA NPs, gelatin NPs, chitosan NPs, PLGA nanospheres, and hydrogel NPs. SLN particles made from solid lipids are submicron colloidal carriers (50-1000 nm) dispersed either in water or in an aqueous surfactant solution. Hydrogel nanoparticles involve self-assembly and self aggregation of natural polymer amphiphiles such as hydrophobized polysaccharides like cholesterol pullulan, cholesterol dextran and agarose where cholesterol groups cross linking points in a non-covalent manner. For example, biodegradable polymeric nanoparticles, typically having polylactic acid (PLA), polyglycolic acid (PGA), polylactic-glycolic acid (PLGA), and polymethyl methacrylate (PMMA), are useful for the delivery of proteins.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition for cold storage of cells comprising a population of isolated stem cells and isolated trophic factors including insulin-like growth factor-1 (IGF-1), a neurotrophin, a tachykinin neuropeptide and a cathelicidin, wherein the isolated trophic factors are in an amount effective to maintain viability and function of the stem cells in the composition at temperatures above 0° C. and below 30° C.

2. The composition of claim 1 wherein the concentration of IGF-I is about 0.3 ng/mL to about 30 ng/mL.

3. The composition of claim 1 wherein the neurotrophin is nerve growth factor-beta (NGF-beta).

4. The composition of claim 3 wherein the concentration of NGF-beta is about 1 μg/L to about 60 μg/L.

5. The composition of claim 1 wherein the neuropeptide is Substance P.

6. The composition of claim 5 wherein the concentration of Substance P is about 1 mg/L to about 5 mg/L.

7. The composition of claim 1 wherein the cathelicidin is bactenecin.

8. The composition of claim 7 wherein the concentration of bactenecin is about 0.5 mg/L to about 50 mg/L.

9. The composition of claim 1 wherein the isolated stem cells are bone marrow stem cells.

10. The composition of claim 1 wherein the stem cells are non-human mammalian stem cells.

11. The composition of claim 1 further comprising a gel or matrix.

12. The composition of claim 11 wherein the gel or matrix is formed of extracellular matrix, fibrin, alginate, or self assembling beta sheet peptides.

13. The composition of claim 1 wherein the isolated stem cells are adult stem cells.

14. The composition of claim 1 wherein the isolated stem cells are embryonic stem cells.

15. The composition of claim 1 wherein the isolated stem cells are cloned stem cells.

* * * * *